Figure 1:
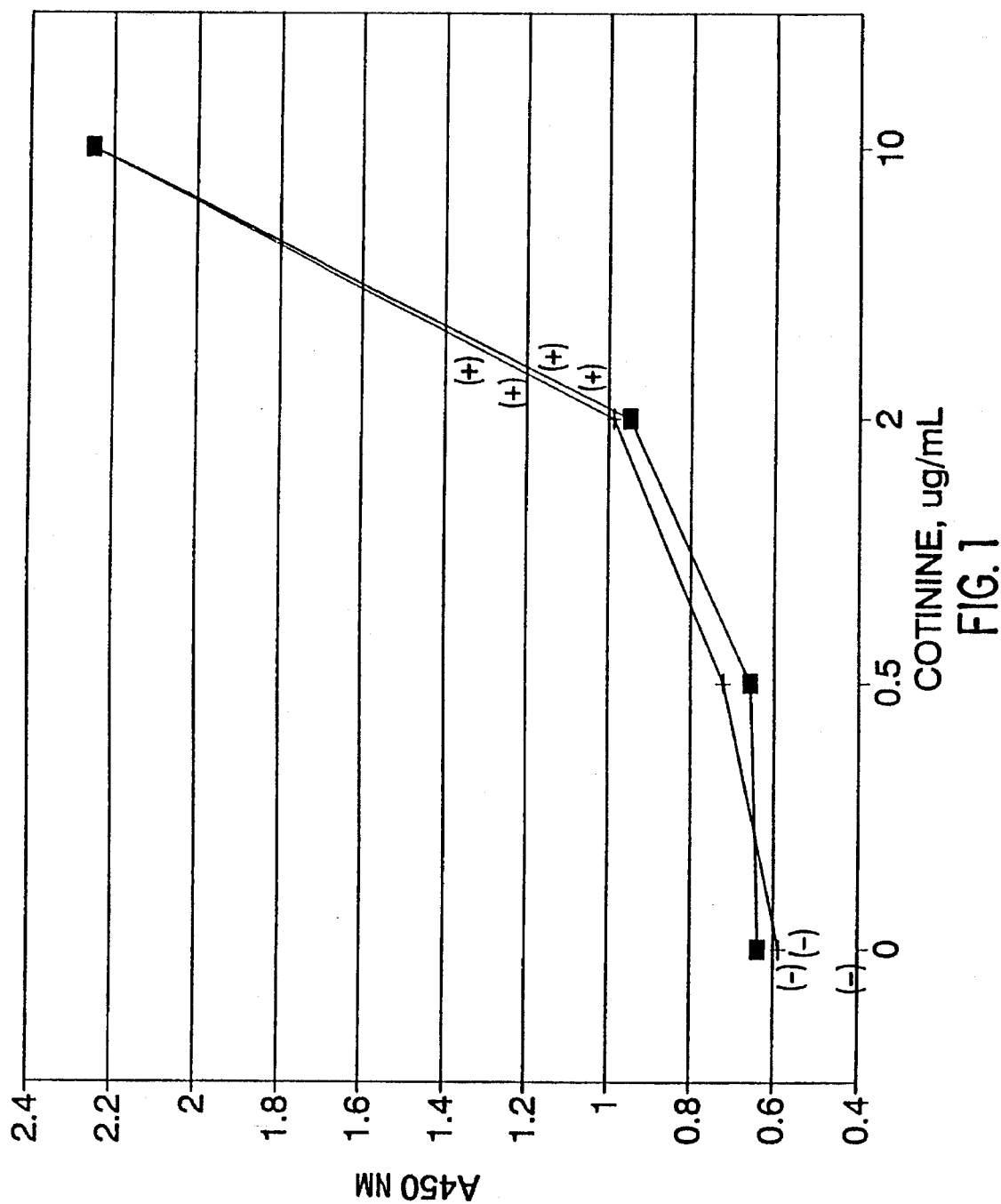

US005527686A

United States Patent [19]

Fitzpatrick et al.

[11] Patent Number: 5,527,686
[45] Date of Patent: Jun. 18, 1996

[54] DIFFERENTIAL BINDING AFFINITIES AND DISSOCIATION ASSAYS BASED THEREON

[75] Inventors: Judith Fitzpatrick, Tenafly; Regina Lenda, Wesley Hills, both of N.Y.

[73] Assignee: Serex, Inc., Maywood, N.J.

[21] Appl. No.: 196,092

[22] PCT Filed: Jul. 29, 1992

[86] PCT No.: PCT/US92/06249

§ 371 Date: Feb. 17, 1994

§ 102(e) Date: Feb. 17, 1994

[87] PCT Pub. No.: WO93/03367

PCT Pub. Date: Feb. 18, 1993

Related U.S. Application Data

[63] Continuation-in-part of Ser. No. 737,526, Jul. 29, 1991, abandoned.

[51] Int. Cl.$^6$ .................................................. G01N 33/535
[52] U.S. Cl. ..................... 435/7.9; 435/188; 435/975; 436/518; 436/525; 436/534; 436/815; 546/278.4
[58] Field of Search .......................... 435/7.2, 7.9, 7.93, 435/6, 975, 188; 436/512, 518, 534, 525, 541, 547, 804, 815, 816; 546/281, 282

[56] References Cited

U.S. PATENT DOCUMENTS

| | | | |
|---|---|---|---|
| 3,817,837 | 6/1974 | Rubenstein et al. | 435/7.9 |
| 4,069,105 | 1/1978 | Singh | 530/363 |
| 4,318,707 | 3/1982 | Litman et al. | 436/537 |
| 4,323,507 | 4/1982 | Leung et al. | 549/231 |
| 4,341,866 | 7/1982 | Yoshida | 435/7.9 |
| 4,434,236 | 2/1984 | Freytag | 436/512 |
| 4,480,042 | 10/1984 | Craig et al. | 436/533 |
| 4,504,413 | 3/1985 | Khanna | 435/188 |
| 4,551,426 | 11/1985 | Freytag et al. | 435/7.92 |
| 4,590,278 | 5/1986 | Edwards, III | 546/281 |
| 4,766,064 | 8/1988 | Williams et al. | 435/6 |
| 4,977,077 | 12/1990 | Ngo et al. | 435/7.92 |
| 5,009,998 | 4/1991 | Chow et al. | 435/7.92 |
| 5,137,808 | 8/1992 | Ullman et al. | 435/7.9 |
| 5,164,504 | 11/1992 | Walling et al. | 546/281 |
| 5,177,021 | 1/1993 | Kondo | 436/518 |
| 5,183,740 | 2/1993 | Ligler et al. | 435/7.32 |
| 5,188,939 | 2/1993 | Mangold et al. | 435/7.92 |

OTHER PUBLICATIONS

Schwartz, et al., 1991, "Accuracy of common drug screen tests", American Journal of Emergency Medicine, 9:166–170.

Mouine, et al., 1990, "Methods of theophylline assay and therapeutic monitoring of this drug", Ann. Biol. Clin., 48:287–293.

Gosling, 1990, "A decade of development in immunoassay methodology", Clin. Chem. 36/8:1408–1427.

Schramm, et al., 1990, "Rapid solid–phase immunoassay for 6–Keto Prostaglandin $F_{1\alpha}$ on microplates", Clin. Chem, 36:509–514.

Kauvar, et al., 1990, "Paralog chromatography", Bio Chromatography, 5:22–26.

Prattis, et al., 1990, "Detection of mouse thymic virus (MTLV) antigens in infected thymus by competition immunoassay", Laboratory Animal Science, 40:33–36.

Barnard, et al., 1989, "Measurement of Estrone–3–glucuronide in Urine by Rapid, homogeneous time–resolved fluoroimmunoassay", Clin. Chem., 35:555–559.

Castro, et al., 1988, "Fluorescence polarization immunoassay for the determination of nicotine", Biochemical Archives, 4:77–84.

Fitzpatrick, 1986, "Purification of antisera to beta human chorionic gonadotropin by a low–affinity chromatography techique", Clin. Chem., 32:1157.

Hinds, et al., 1985, "Ligand displacement immunoassay—demonstration of its use for the measurement of serum phenobarbital and phenytion", Clinica Chimica Acta, 149:105–115.

Hinds, et al., 1984, "Ligand displacement immunoassay: a novel enzyme immunoassay demonstrated for measuring theophylline in serum", Clin. Chem., 30:1174–1178.

Kulpmann, et al., 1984, "Determination of total and free phenytoin in serum by non–isotopic immunoassays and gas chromatography", J. Clin. Chem. Clin. Biochem., 22:773–779.

Hankins et al., "Pyrrolidine–Substituted Nicotine Analogs:Synthesis and Pharmacology", J. of Pharmaceutical Sciences, vol. 59, No. 3, (1970), pp. 342–344.

Langone et al., "Nicotine and its Metabolites, Radioimmunoassays for Nicotine and Cotinine", Biochemistry, vol. 12, No. 24, (1973), pp. 5025–5030.

Primary Examiner—Toni R. Scheiner
Assistant Examiner—Susan C. Wolski
Attorney, Agent, or Firm—Klauber & Jackson

[57] ABSTRACT

A method for assaying for the presence of analyte in a sample based on differential binding affinity involves detecting dissociation of a complex of receptor and ligand in the presence of analyte. The receptor binds the analyte with high affinity and with the ligand with low affinity. The receptor-ligand complex may be formed in situ or may be preformed. In the presence of free analyte, the receptor releases from the receptor-ligand complex and binds free analyte. Release of the receptor-ligand complex is detectable. A kit for performing release assays to detect the presence of analyte is also provided.

20 Claims, 14 Drawing Sheets

DIFFERENTIAL BINDING AFFINITIES AND DISSOCIATION ASSAYS BASED THEREON

This application is a continuation-in-part of application Ser. No. 07/737,526, filed Jul. 29, 1991, now abandoned.

1. FIELD OF THE INVENTION

The present invention relates to methods for determining the presence of an analyte in a sample. More particularly, homogeneous liquid-phase and heterogeneous liquid-phase/solid-phase release assays that are highly specific and sensitive are provided.

2. BACKGROUND OF THE INVENTION

Immunoassays utilize the specific binding capabilities of antibodies to detect the presence of target molecules in solution. Although the general principle is applicable to a broad range of problems, major commercial interest has centered on medical diagnostic applications for a wide variety of analytes in biological fluids such as blood, saliva, and urine.

Several types of immunoassays, useful for distinct applications, already exist. Each such assay type requires a way of distinguishing whether binding sites on an antibody are occupied or free. Typically this is accomplished by means of label such as an atom, molecule, enzyme or particle attached permanently to either the antibody or to an analog of the analyte.

Sensitivity and specificity are key parameters of an immunoassay. Specificity relates primarily to the antigen binding site of the antibody, which is inherent to selection of variable region gene segments and is independent of the assay configuration. Sensitivity relates primarily to the affinity of the antibody for its ligand(s) and to the inherent detectability of the label. For example, radioisotopes, used for radioimmunoassay, can be detected at significantly lower concentrations than fluorescent molecules. Enzyme labels are detectable at concentrations similar to fluorescent labels. When substrates that produce fluorescent or chemiluminescent products are used with enzyme labels, the sensitivity of resulting immunoassays is comparable or greater than with radioisotope labels.

Many conventional assay techniques are considered competitive in that the analyte and labeled component have comparable affinities of the antibody binding site. One example of such a competitive method is found in U.S. Pat. No. 3,817,837 by Rubenstein and Ullman which describes a technique in which ligand and enzyme-bound-ligand compete for antibody binding sites. Since binding of the antibody to the enzyme-bound-ligand alters its enzymatic activity, the concentration of ligand present can be estimated by measuring the rate at which such a mixture converts substrate to product.

Immunoassays can be further characterized as homogeneous and heterogeneous. In a heterogeneous method, the label is equally detectable in bound and unbound states. To obtain any meaningful assay results physical separation of the bound versus unbound antibody is required. A common strategy for accomplishing this separation entails associating the label to a solid phase which can be physically separated from the liquid phase prior to the detection step. A typical heterogeneous assay is the Tandem EIA from Hybritech, Inc.

In a homogeneous method, the detectable property of the label is inherently different depending on whether bound or unbound. In its bound state, the label will haver greater or lesser signal intensity. Usually, binding of antibody to the labeled ligand causes a decrease in signal intensity, e.g., when the label is an enzyme. Typical products in this category include the EMIT line of enzyme immunoassays from Syva Company and the TDX line of fluorescence polarization immunoassays from Abbott Diagnostics.

Two further characteristics of immunoassays are particularly noteworthy. These are the minimal concentration of analyte that can be detected, and the dynamic range of detection. The dynamic range is the range of analyte concentrations over which signal from a label changes from zero to maximum. The order in which the sample, the antibody, and a labeled component are combined can significantly affect both of these key parameters by affecting the degree of binding of the labeled component, which in turn affects detection of the label.

In certain known assay methods, the antibody and the analyte are combined prior to addition of the labeled component. In others, the analyte and labeled component are combined prior to addition of the antibody. Each of these cases requires providing two separate reagents that are combined with the sample containing the analyte. The need for two such separate reagents can be inconvenient and result in a more cumbersome, complex method. Moreover, because precise volumetric measurement of each reagent is critical to good assay performance, the necessity of two measuring steps can cause errors which may lead to distorted results.

One method to improve assay precision and thereby enhance assay sensitivity is to provide a premixed complex of the antibody and labeled component. This is problematic, however, because the binding reaction is generally found to be irreversible. Thus, when a complex of the labeled analyte and antibody are combined with a solution containing the analyte, no appreciable displacement of bound label occurs in a meaningful time frame (seconds to minutes).

The present invention relates to assay methodology that employs a complex of receptor and a ligand, wherein the receptor-ligand complex dissociates in the presence of an analyte and a stable receptor-analyte complex is formed. Dissociation of the receptor-ligand complex in the presence of analyte is detectable thereby positively indicating the presence of analyte in a test sample. Methods for designing, preparing, using, and stabilizing such complexes are taught. The methodology is applicable both to homogeneous assays and heterogeneous assays for analytes encompassing a broad range of types and sizes.

3. SUMMARY OF THE INVENTION

The present invention provides for heterogeneous and homogeneous release assay methods for detecting the presence of an analyte in a sample. A kit for performing the assay method of the invention is also provided.

According to the present method, a test sample is contacted with a receptor-ligand complex. The receptor has much a higher association constant for analyte than ligand. When the receptor-ligand complex dissociates into its receptor and ligand components in the presence of free analyte in the test sample, receptor binds the free analyte to form a stable receptor-analyte complex, which is substantially unaffected by the presence of free ligand. In accordance with the present method, dissociation of the receptor-ligand complex, i.e., release of the receptor and ligand, is a detectable event indicating the presence of analyte in the test sample. Detection of either dissociated ligand or receptor is contemplated.

Means for detection are detailed infra in sections 5.2, 5.2.1 and 5.2.2.

In one embodiment of the invention a kit for carrying out the present method is provided. The kit includes either preformed receptor-ligand complex or receptor and ligand which are mixed to form the complex prior to conducting the assay. As can be appreciated, when the pre-formed complex is provided, apart from test sample, only this single reagent may be required to carry out the assay.

As shown in the Examples, infra, the present invention provides surprisingly greater sensitivity, specificity, accuracy and range of detection than conventional association assays or competitive dissociation assays.

3.1. Definitions

Analyte—molecule of interest in an assay.

Ligand—molecule capable of binding to a receptor specific for analyte with substantially lower affinity than that of analyte binding to the receptor.

Receptor—molecule capable of specifically binding to analyte or ligand. In each case, a stable complex is formed, but the association constant of receptor for analyte is higher than that for ligand. Dissociation of the receptor-ligand complex into its receptor and ligand components in the presence of free analyte results in release of the receptor which binds to free analyte, thereby forming a stable receptor-analyte complex substantially unaffected by the presence of free ligand.

4. BRIEF DESCRIPTION OF THE DRAWINGS

FIG. 1. Release of anti-cotinine antibody in the presence of cotinine in a urine matrix sample. Anti-cotinine was labeled with peroxidase and complexed with solid phase cotinine ligand. Free cotinine was added and released anti-cotinine was detected by measuring enzyme activity in the supernatant after 2 min incubation. Ligands were cotinine conjugated to BGG, using the linker aminocaproic acid (open squares) or p-aminobenzoic acid (solid squares).

Figure 2:
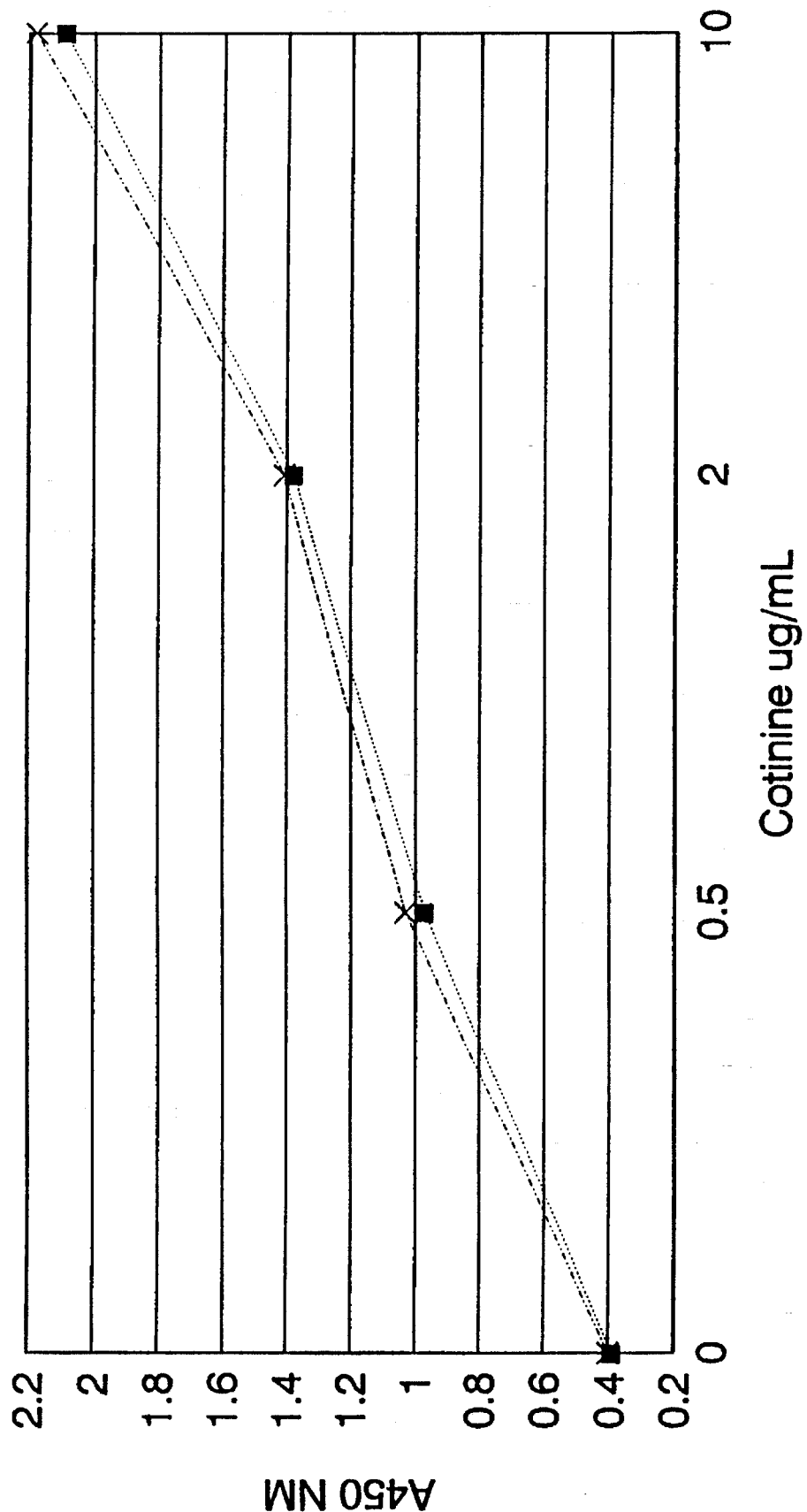

FIG. 2. Release of anti-cotinine antibody after a 10 minute incubation in a complex with immobilized ligand. A synthetic urine matrix sample was spiked with cotinine. Ligands are the same as for FIG. 1.

Figure 3:
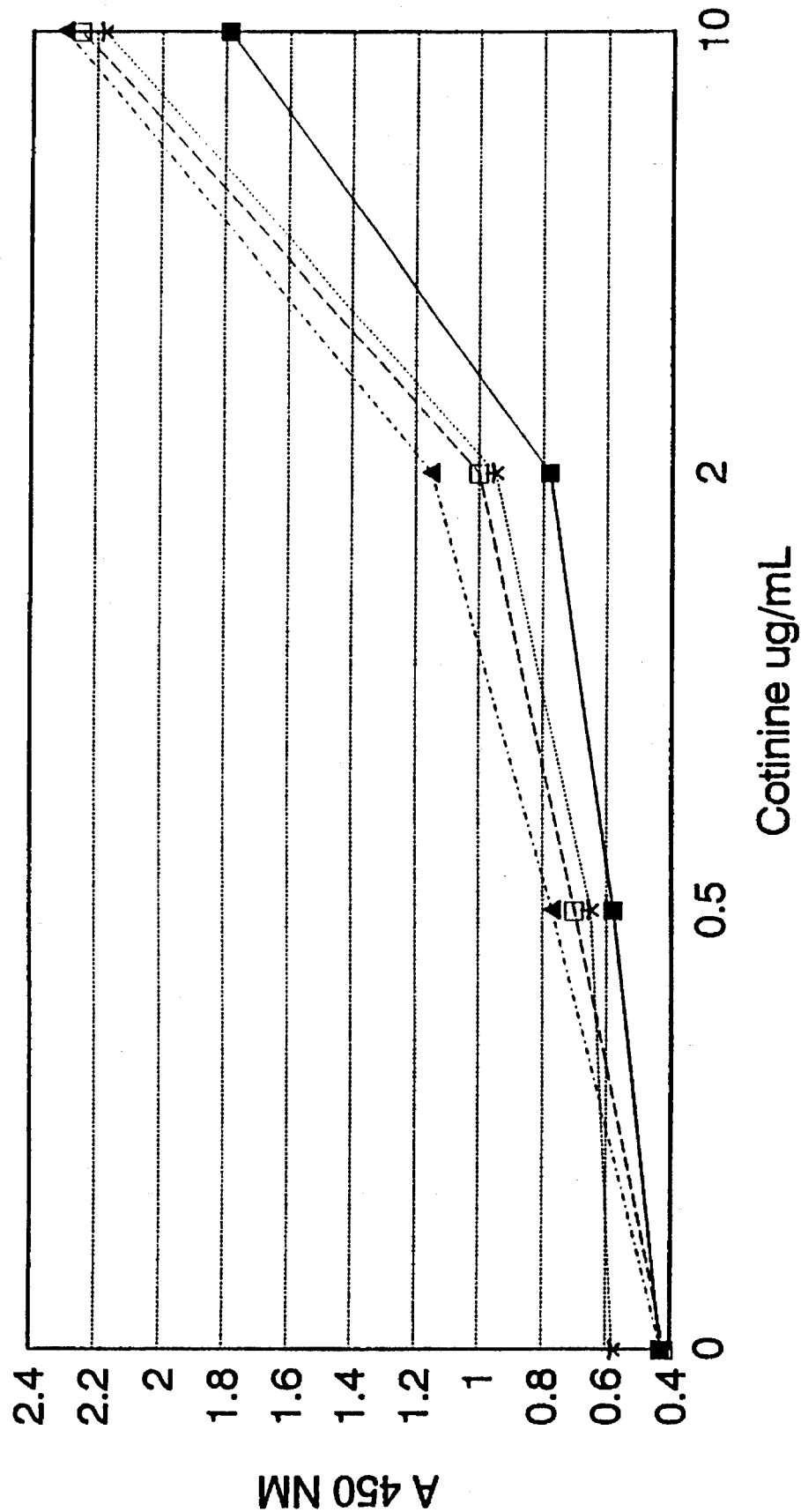

FIG. 3. Release of anti-cotinine antibody after a 2 minute incubation in urine and synthetic urine matrix samples. Release of labeled anticotinine was detected from cotinine-aminocaproyl-BGG in urine (solid squares) and synthetic urine (open squares) and from cotinine-benzoyl-BGG in urine (asterisks) and synthetic urine (solid triangles).

Figure 4:
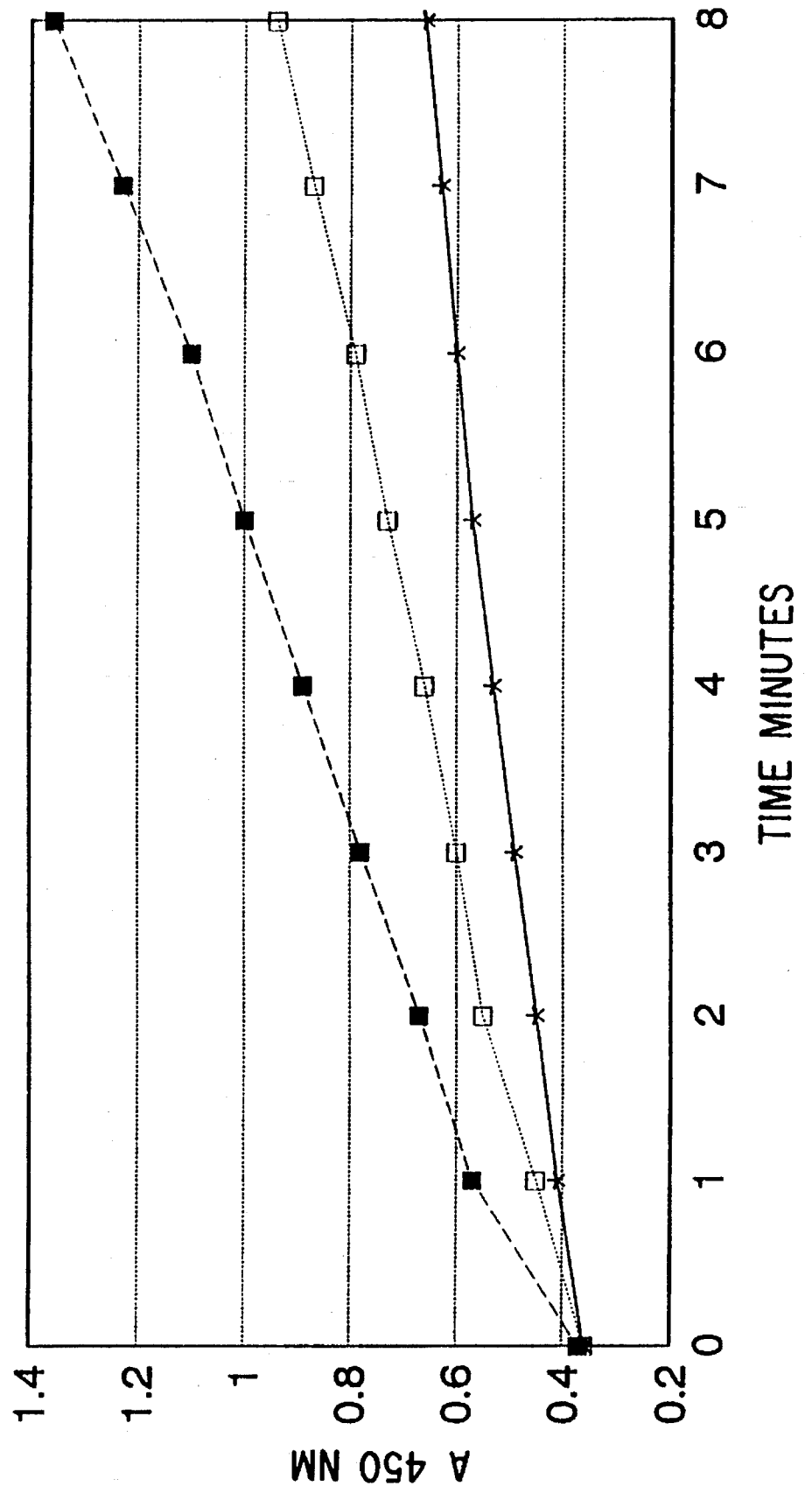

FIG. 4. Deactivation and inhibition of a glucose-6-phosphate dehydrogenase-hydroxycotinine conjugate. Normal enzyme activity (solid squares), conjugate activity (open squares), and conjugate activity in the presence of antibody (asterisks) are shown.

Figure 5:
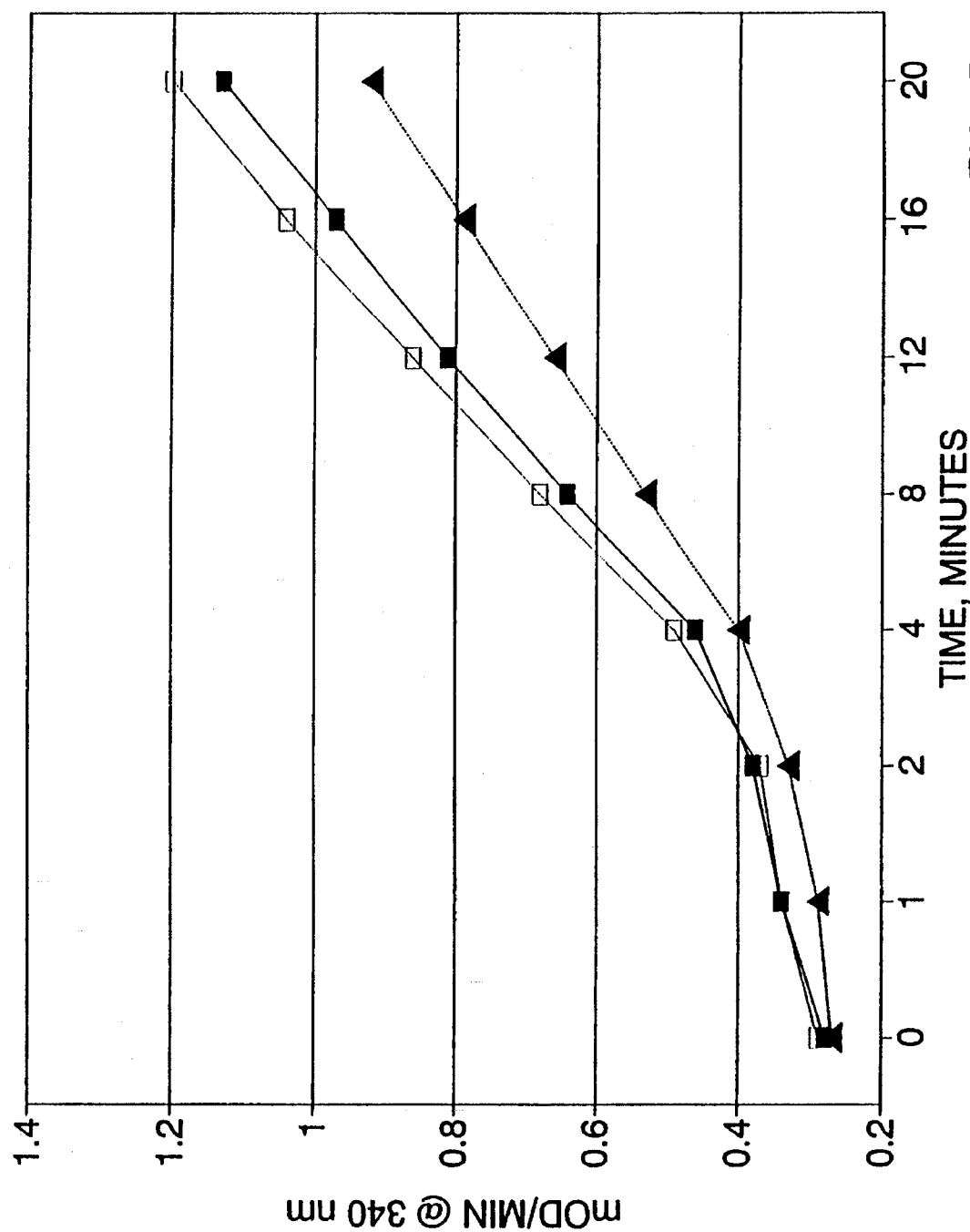

FIG. 5 Inhibition and release of a hydroxycotinine-glucose-6-phosphate dehydrogenase conjugate. The enzyme activity ($A_{340}$ vs time) of enzyme conjugate (solid squares), enzyme conjugate plus antibody to cotinine (solid triangles), and enzyme conjugate+antibody+free cotinine (open squares) are shown.

Figure 6:
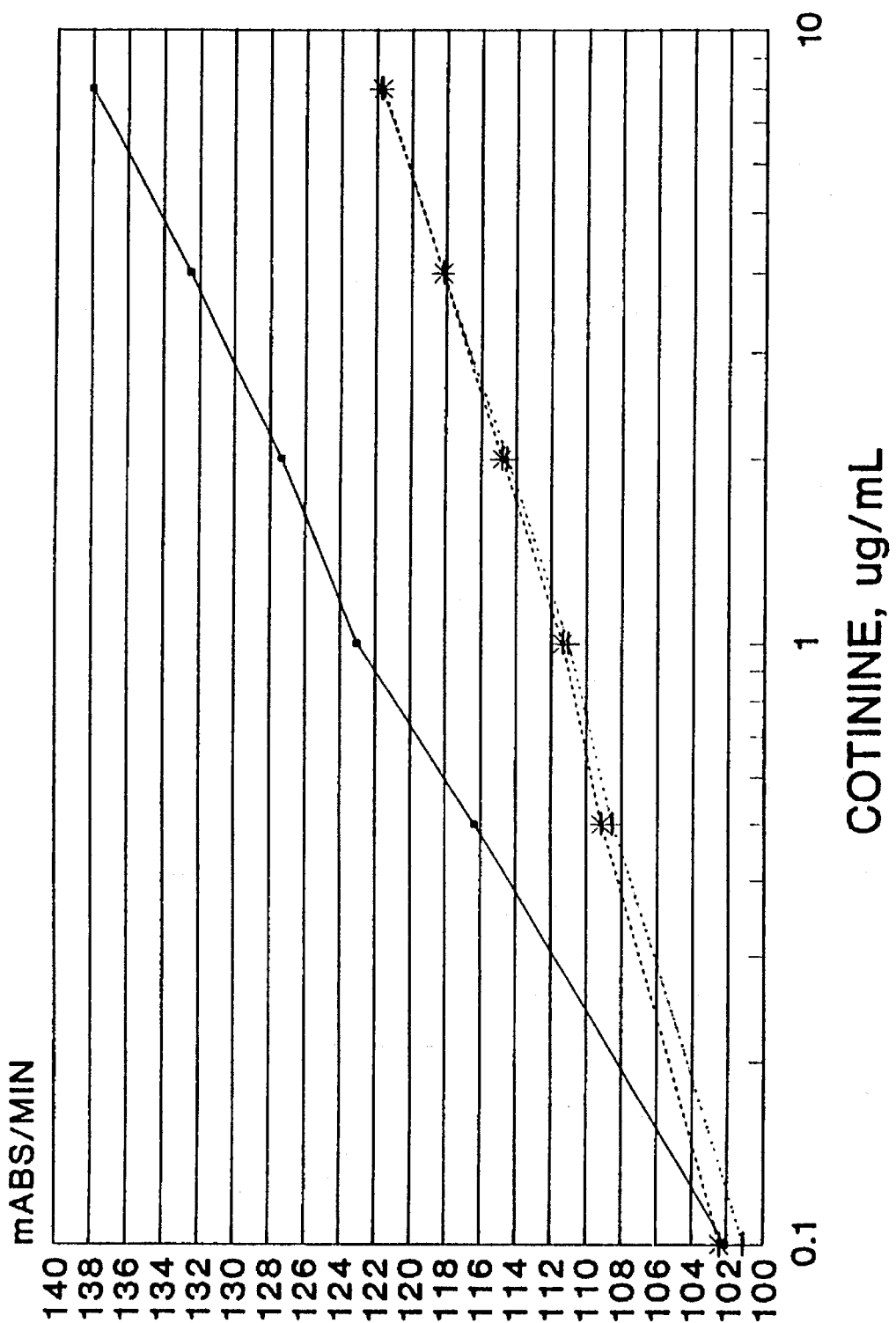

FIG. 6. Automated release assay for cotinine. Release in the presence of cotinine was measured on an automated analyzer after <1 (dots), 18 (crosses), and 22 (asterisks) hours of complex incubation.

Figure 7:
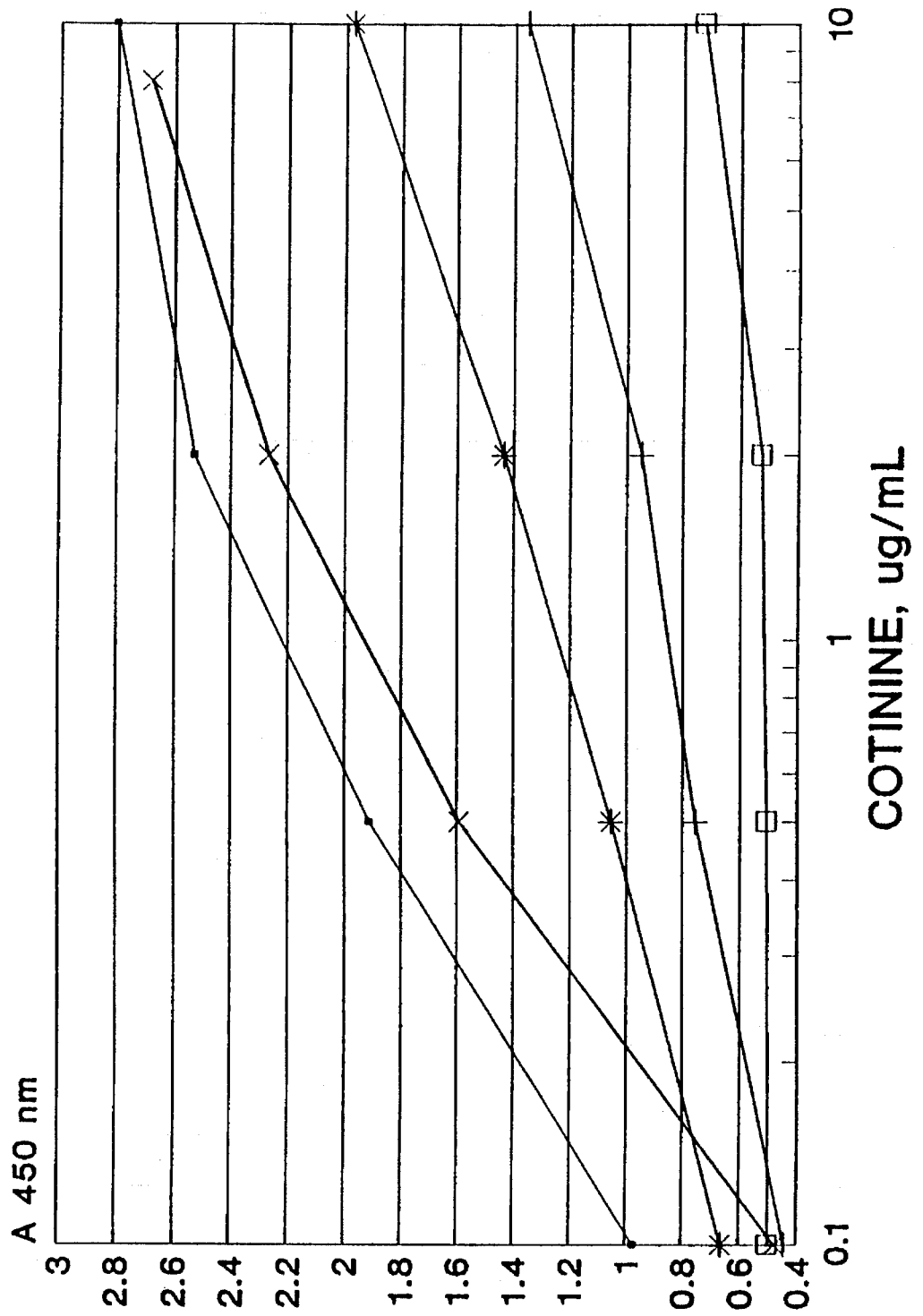
Figure 8B:
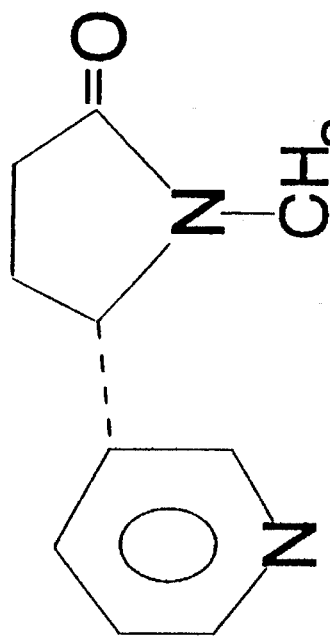
Figure 8D:
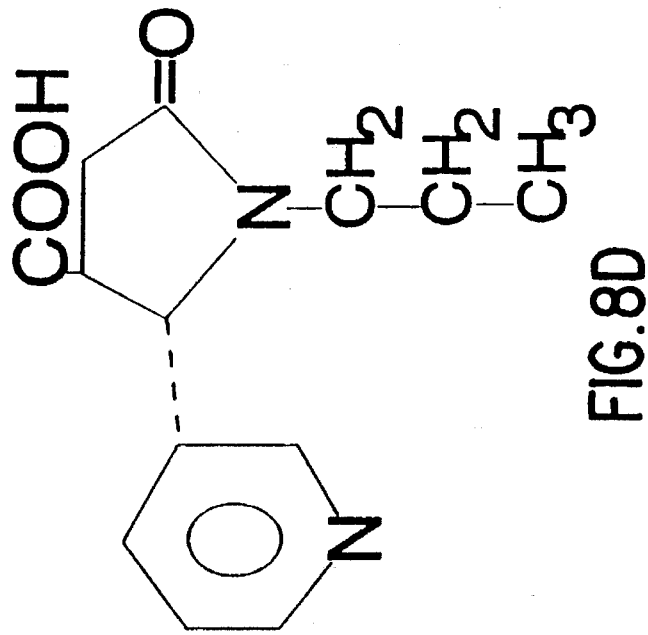
Figure 8A:
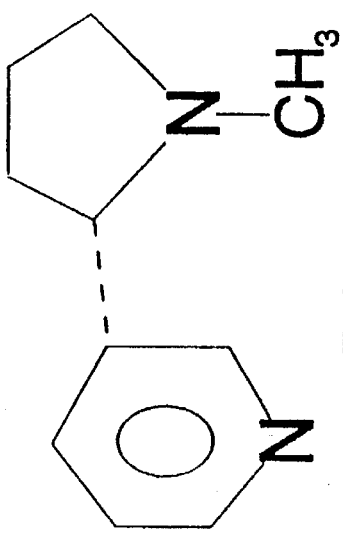
Figure 8C:
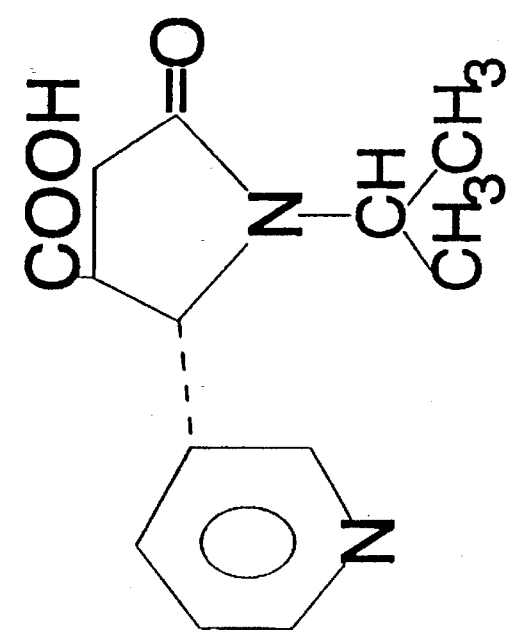

FIG. 7. Efficiency of various low affinity analogs of cotinine conjugated to glucose-6-phosphate dehydrogenase. Conjugates of trans-hydroxy cotinine (extensively conjugated (dots), or partially conjugated (vertical lines, asterisks)), cis-hydroxycotinine (crosses) and carboxycotinine (open squares) to glucose-6-phosphate dehydrogenase were tested as release ligands in a solid phase assay.

FIG. 8. Structure of (a.) nicotine, (b.) cotinine, (c.) N-isopropyl-4-carboxy-norcotinine and (d.) N-Propyl-4-carboxy-norcotinine.

Figure 9:
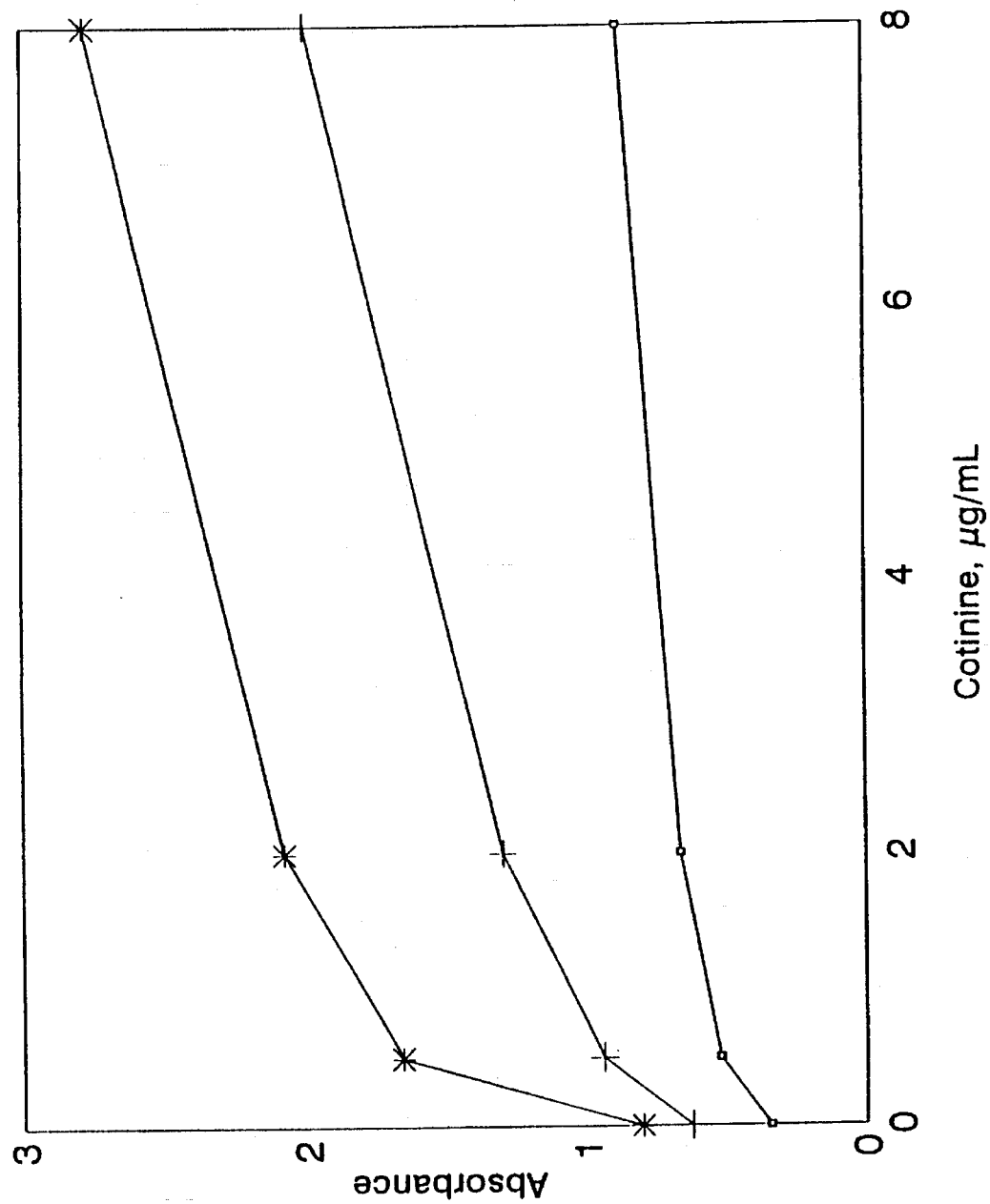

FIG. 9. ELISA format release assay. Microtiter plates were coated with cis hydroxycotinine G-6-PDH (asterisks); N-isopropyl-norcotinine G-6-PDH (plus signs); N-propyl-norcotinine G-6-PDH [open stippled squares].

Figure 10:
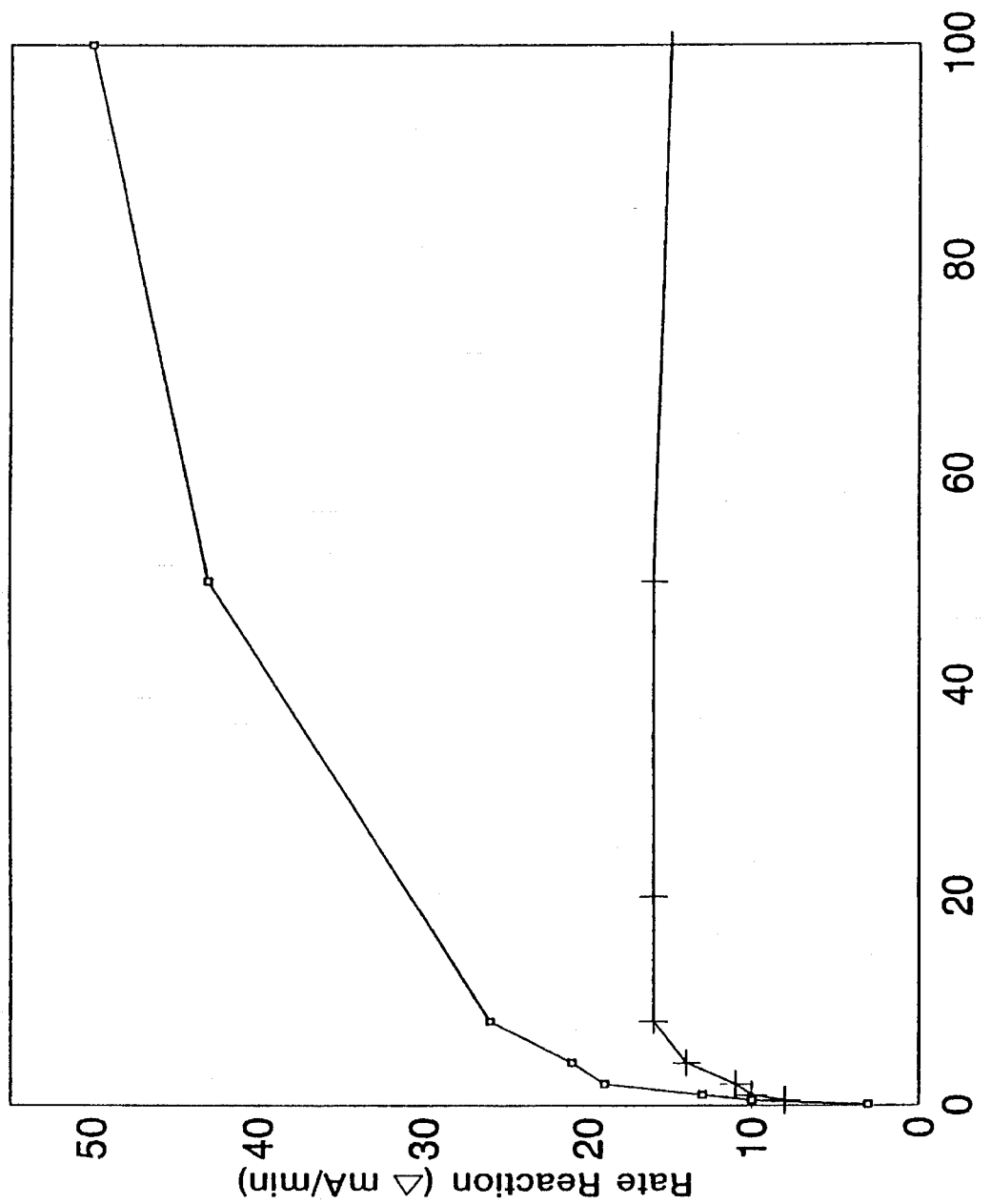

FIG. 10. Comparison of the dose response curves of an associative homogenous assay for cotinine (NiMA) with the release assay. Associative NiMA assay (plus signs); release assay (open stippled square).

Figure 11:
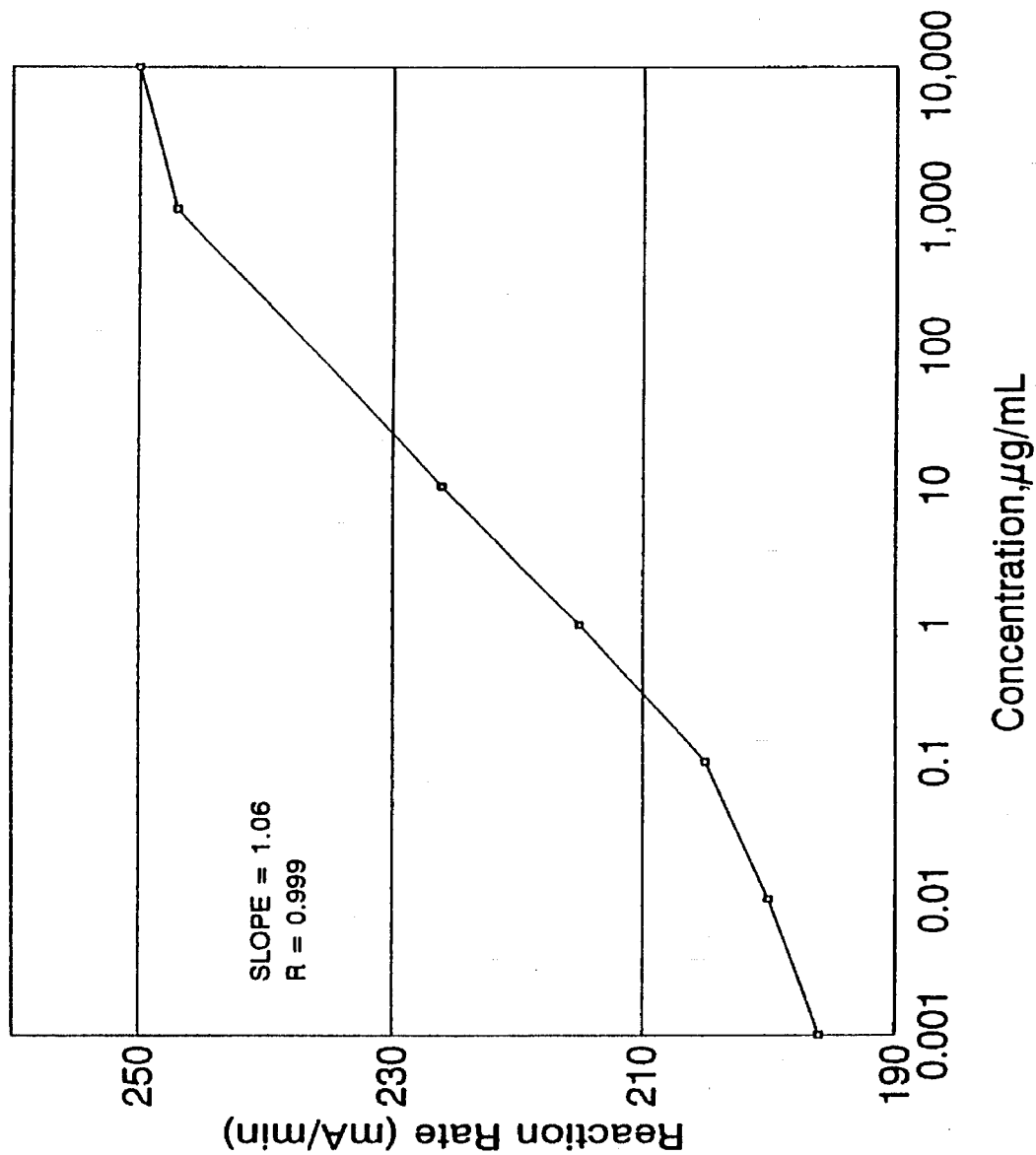

FIG. 11. Standard curve for the release assay of cotinine by the homogeneous method.

Figure 12:
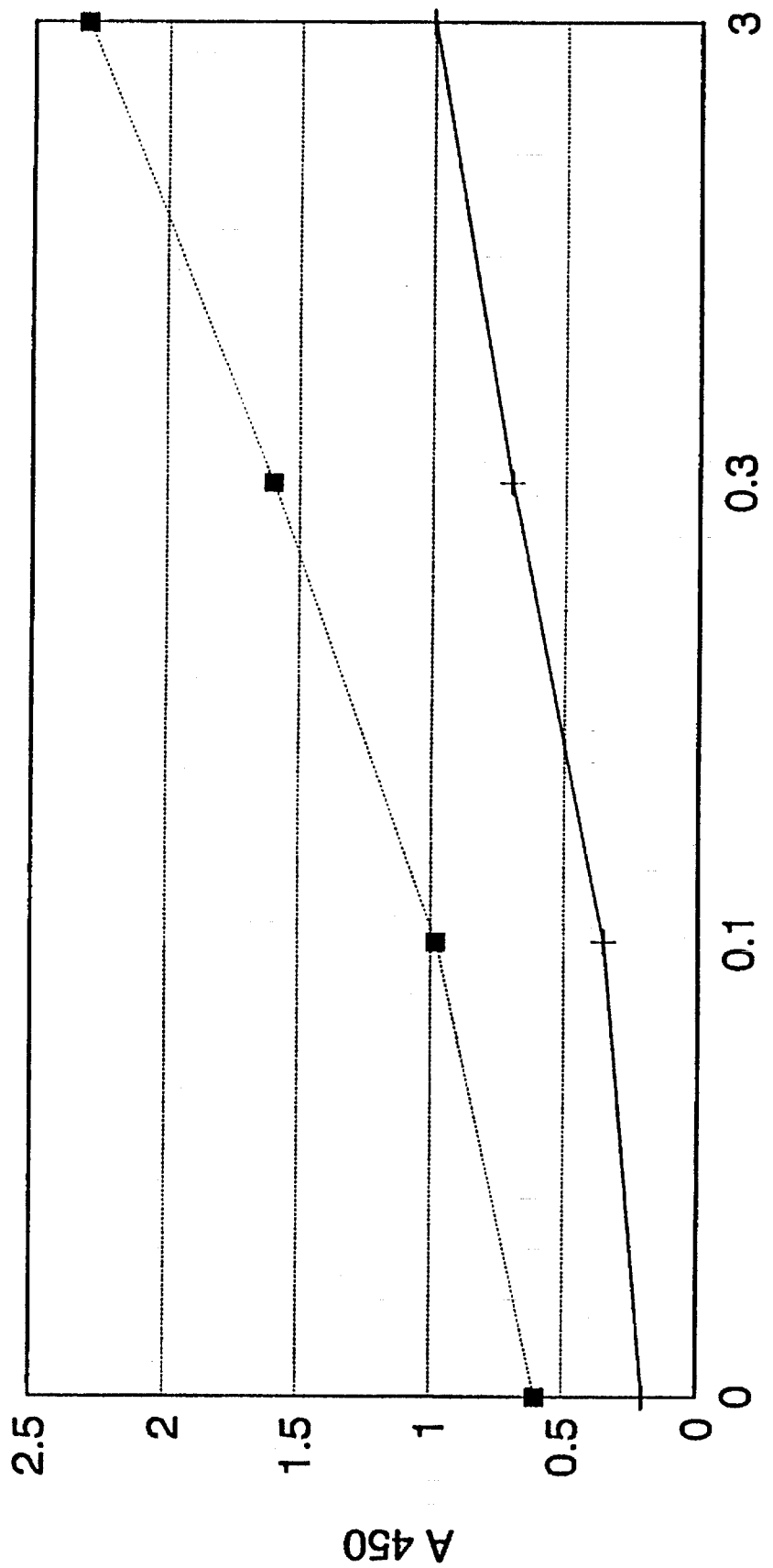

FIG. 12. Benzoylecgonine release assay using a microtiter plate format. Matrix effects were observed depending on the liquid medium, which was either water (solid squares) or urine (crosses). BE is benzoylecgonic.

Figure 13:
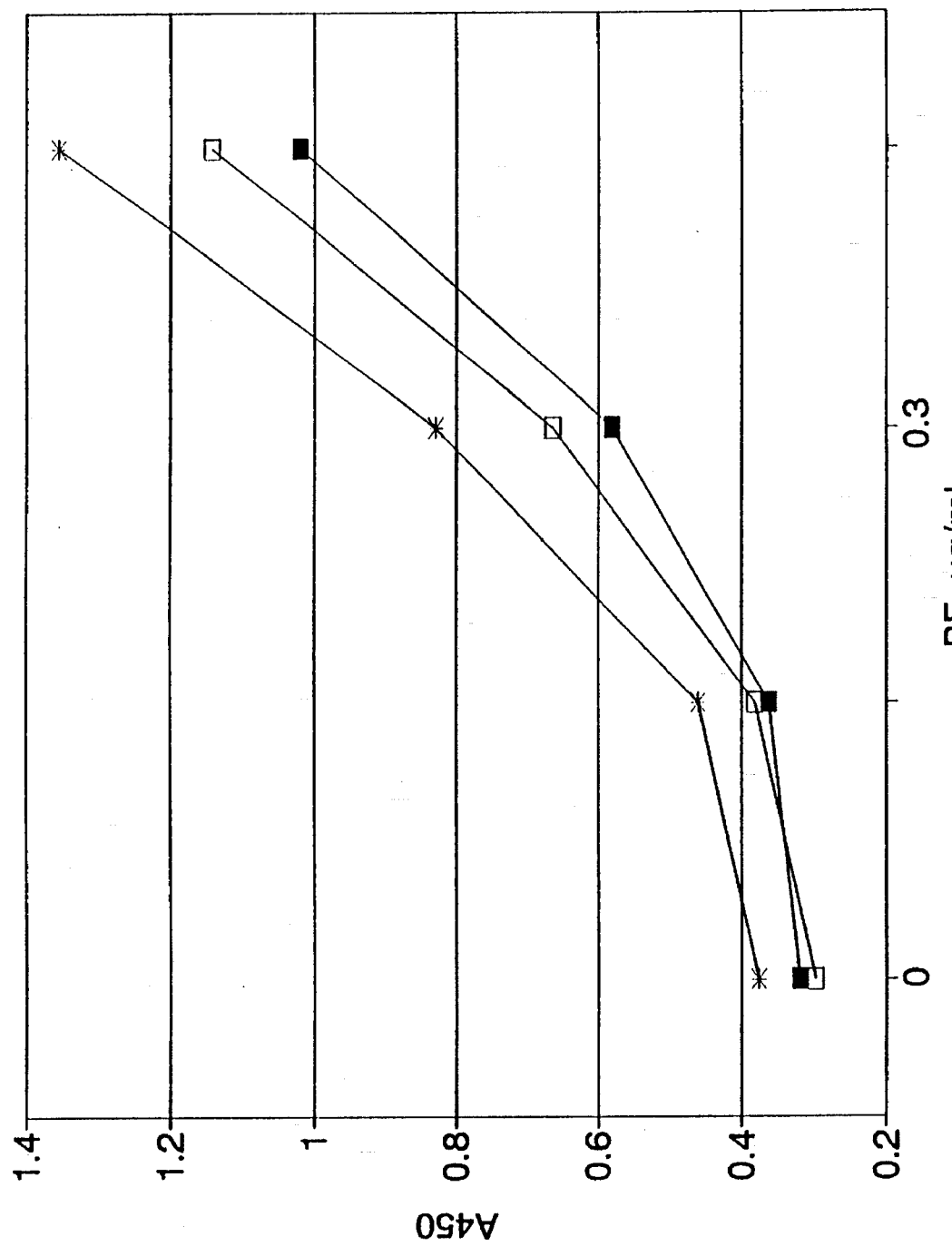

FIG. 13. Effect of incubation time on benzoylecgenine release assay using a microtiter plate format. Supernatants were obtained 0 (solid squares), 2 (open squares) and 10 (asterisks) minutes after addition of free benzoylecgonine (BE) and checked for release of labeled anti-benzoylecgonine.

Figure 14:
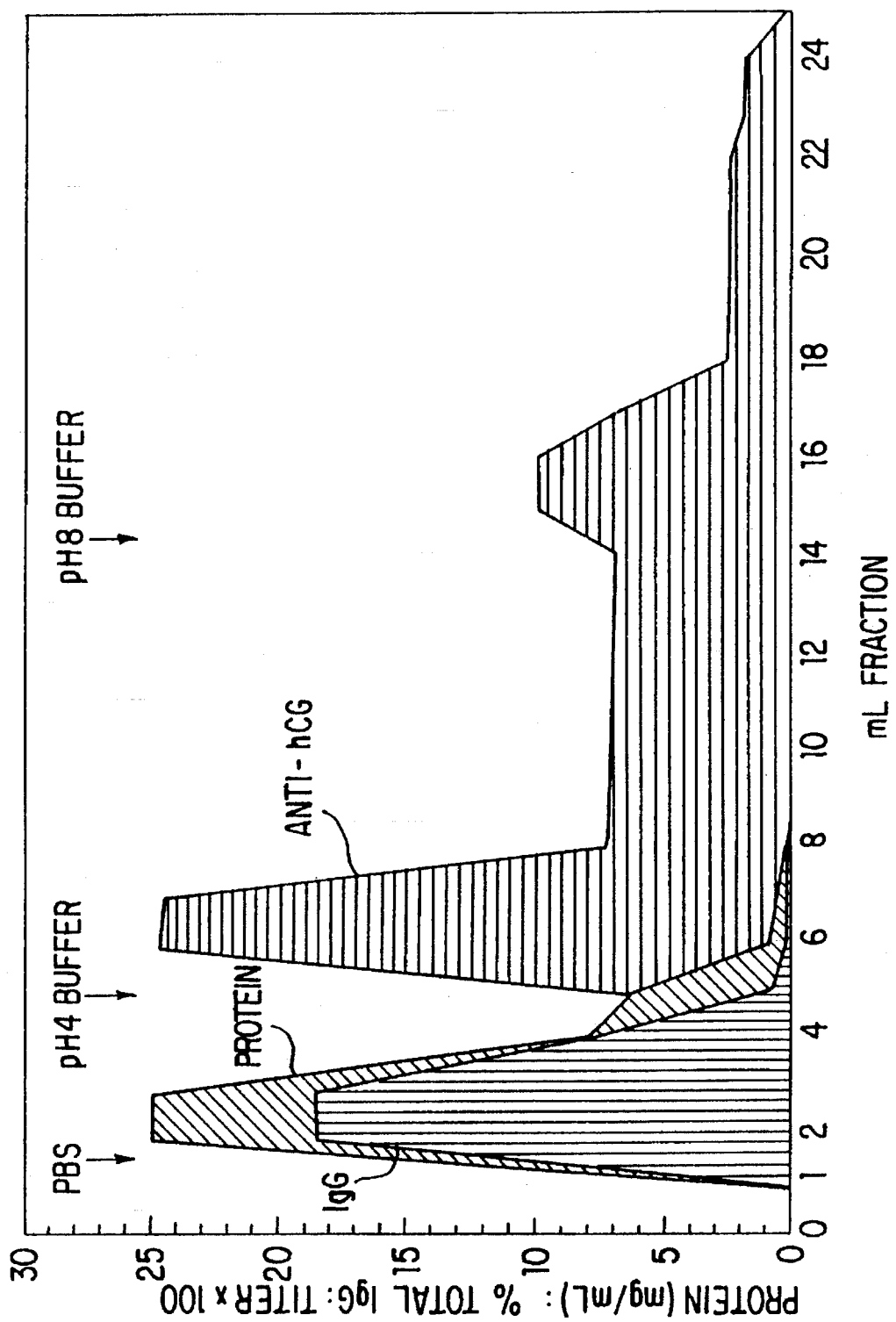

FIG. 14. Low affinity chromatography of anti-beta hCG. Rabbit antiserum to human chorionic gonadotropin (hCG) was applied to a sheep gonadotropin affinity column and eluted with 13 ml PBS, 20 ml of pH 4 buffer, and 10 ml of pH 8 buffer. Protein (light cross-hatch); anti-hCG (dark cross-hatch); IgG (double cross-hatch).

5. DETAILED DESCRIPTION OF THE INVENTION

In accordance with the present invention a method for detecting the presence of analyte in a sample and kits therefore are provided. A test sample can be any body fluid, such as urine, blood, serum, saliva, bodily exudate, etc., suspected of containing the target analyte. The release assay method of the invention involves contacting a test sample with a receptor-ligand complex and, if analyte is present, detecting dissociation of that complex into its receptor and ligand components. Dissociation of the complex in the presence of analyte results in release of receptor and ligand. Upon release, receptor binds with free analyte, forming a receptor-analyte complex that remains stable in the presence of free ligand. Either dissociated ligand or receptor can be detected to indicate the presence of analyte in the sample. The assay method of the invention may be performed in either homogeneous or heterogeneous formats. Specific details of each format are provided infra in Section 5.2.

A release assay of the present invention allows preparation of a complex in which receptor binding sites and ligand are present in approximately equal concentration, i.e., quantitative complex formation, although this is not essential. Having each element present in equal concentration enhances sensitivity, since when receptor is present in excess, it can bind analyte without releasing from receptor-ligand complex.

In, order to achieve a receptor-ligand complex in which the number of binding sites of each element are present in substantially equimolar amounts, the receptor and ligand are incubated for at least ten seconds prior to exposure to sample. Preferably the incubation time is greater than about one hour. A long incubation time allows formation of the most stable complexes during repeated release and binding reactions when one element, either receptor or ligand, is present in excess. After the low affinity binding reaction reaches equilibrium, the receptor-ligand complex is isolated from the excess element. Isolation of the complex may be either by size exclusion chromatography, density gradient centrifugation, low affinity chromatography, or other techniques for separating complexes from their components. Alternatively, the receptor and ligand may be mixed in equal binding site concentrations and incubated to allow substantially quantitative binding to create stable complexes. Formation of the reagent-ligand complex is discussed more fully in Section 5.1., infra.

The kit of the present invention preferably includes preformed receptor-ligand complex, thereby eliminating the need to prepare reagents prior to conducting an assay. However, providing both receptor and ligand separately, and mixing them prior to the assay, is within the scope of the invention.

The present invention is based on the principle that dissociation of a complex of receptor and ligand in the presence of analyte will result in association of receptor and analyte rather than reassociation of receptor and ligand when the association constant of receptor and analyte is greater then the association constant of receptor and ligand. The dissociation of a receptor-ligand complex, release of receptor and ligand, and binding of receptor to analyte to form a stable complex is termed herein the release reaction. The corollary of a release reaction is that free ligand will not affect the stability of the receptor-analyte complex, so that the receptor will not bind to free ligand, i.e., the release reaction is not reversible. Similarly a stable receptor-ligand complex will not dissociate and release receptor to bind a second low affinity cross reactive ligand because there is no kinetic or the thermodynamic gain. The dissociation constant of even a low affinity receptor-ligand complex is relatively low, and binding to another ligand with an equivalent affinity constant does not result in a free energy change. This results in a sensitive, highly specific, highly accurate (minimally cross reactive) assay.

However, when analyte binds receptor with high affinity and the association constant is high, dissociation of the receptor from the receptor ligand complex and binding to the analyte will occur readily. The high association rate will result in fast "pickup" of dissociated receptor. The release reaction is thermodynamically favorable, since a higher affinity constant will give a negative net free energy change. The thermodynamics and kinetics will drive a release reaction in the presence of analyte, and will result in no change in the absence of analyte.

Preferably the affinity constant of binding of receptor to ligand will be about 10%, and more preferably about 1%, of the affinity constant of binding of receptor to analyte. This can be observed qualitatively as relative binding, e.g., by apparent activity in an assay.

Because the thermodynamics and kinetics of the release reaction favor binding of receptor to analyte over binding of receptor to ligand, macroscopically analyte appears to induce the release reaction, i.e., dissociation of the receptor-ligand complex.

Since the release reaction depends on a high affinity association of receptor and analyte, it is sensitive and specific. That is, receptor will bind low concentrations of analyte. Dependence of the release reaction on the differential affinity binding further increases specificity. Receptor will not dissociate and bind cross-reactive analogs of the analyte unless the binding constant is much higher than the binding constant of receptor and ligand.

It is important to emphasize that a significant portion of the complex must dissociate, or the background "noise" in the system will be too great. For example, if only 1% of the receptor-ligand complex is dissociated, 99% of the system is unaffected. If the standard deviation of measurement is 1% (equivalent to 99±1%), which represents an excellent coefficient of variation in immunoassay systems, then the effect of 1% release would be 1% ±1%, nullifying any significance. By taking advantage of the thermodynamic and kinetic impetus of the release reaction, the present assay provides for significant dissociation of receptor-ligand complex, i.e., release above the baseline levels. Moreover, the release assay format provide for a broad concentration range over which analytes can be detected.

The receptor-ligand complex need not be fully dissociated for effectiveness, however. For example, when a solid phase preparation of hydroxycotinine linked to a carrier protein (e.g., glucose-6-phosphate dehydrogenase) is reacted with sample, only 5–10% of total antibody labeled with the enzyme horseradish peroxidase is displaced by analyte. The exact percentage is difficult to ascertain since enzyme activity on a solid phase is known to be less than that of enzyme in liquid phase. Nevertheless, the amount of release (greater than 5%) provides a significant signal over background. In a homogeneous release assay, the sample containing cotinine induces 100% reversal of enzyme inhibition, which indicates 100% release.

5.1. The Receptor-Ligand Complex

An effective release assay requires formation of a stable low affinity receptor-ligand complex at equilibrium. This complex usually forms more slowly than conventional complexes, e.g., receptor-analyte, or antibody-antigen complexes, etc. Dissociation occurs readily during initial receptor-ligand complex formation. However, after a suitable incubation period, the receptor-ligand complex becomes stable. The stability of the complex is in part a function of the design of the ligand, as well as incubation time of ligand and receptor. The appropriate incubation time is readily determined for each receptor and ligand combination. Generally, however, receptor and ligand should be incubated at least 10 seconds, preferably at least 10 minutes, and more preferably longer than 1 hour, prior to exposure to analyte. In cases where the receptor-ligand complex is isolated prior to performing the assay, both receptor and ligand binding sites are present in substantially equimolar amounts and the incubation time is not important (see Section 5, supra). Under appropriate conditions, e.g., the presence of salts such as sodium chloride, or stabilizing agents such as glucose, or both, the stable receptor-ligand complex will remain releasable over a long time period—days, weeks or longer. According to the present invention, a stable receptor-ligand complex may be in solution, or it may be dried. In an Example, infra, a release astray could be run six days after antibody-ligand complex formation in the presence of 5% sodium chloride. In another Example, infra, the presence of glucose stabilized a dry antibody-ligand complex.

Although the present invention is not bound by any theory or hypothesis, it is believed that formation of a stable receptor-ligand complex supports a model of molecular accommodation between the ligand and the receptor. The equilibrium of this binding favors a configuration of the complex which stabilizes it, meaning that the effective affinity of the complex may, and probably must be, higher in the mature complex than initially. Only by creating a stable complex can one assure that dissociation is specific, and is driven by the much higher affinity of the receptor for the analyte.

Unless a release type assay is formatted with differential binding affinities, and preferably includes the use of stabilizing agents, undesirable irreversible receptor-ligand complex formation can occur. For example, in a conventional homogeneous immunoassay, if the complex between antibody and ligand labeled with enzyme is allowed to remain in solution overnight, the enzyme is gradually denatured. Evidently molecular accommodation of the antibody-ligand complex generally occurs in such a way as to denature the enzyme rather than producing only reversible inhibition.

The present invention overcomes these limitations. Continuing with the example of an enzyme label, in the release system, incubating a complex in the presence of high salt to prevent formation of an unreleaseable receptor-ligand complex, in which ligand or receptor is labeled with enzyme, preserves the enzyme activity as well as the ability to dissociate the receptor-ligand complex. When ligand is labeled with enzyme, using a molecular linker helps position the receptor such that formation of the complex does not denature the label, e.g., enzyme, for at least several days.

5.1.1. Receptors

One element of the receptor-ligand complex is a receptor having one or more binding sites capable of specifically binding to analyte, in which the association constant of binding is high. The receptor is also capable of binding to ligand with an association constant of binding relatively low compared to that of receptor binding to analyte. Suitable receptors for use in release assays of the invention include nucleic acid molecules (RNA or DNA), antibodies (or a fragment of the antibody that contains the analyte binding site for analyte and ligand), cell surface receptors (or a fragment of a cell surface receptor that contains the binding site for analyte and ligand), enzymes (or the substrate binding site of an enzyme), lectins or any other molecule or macromolecule capable of specifically binding to and forming a stable low affinity complex with a ligand and a stable high affinity complex with an analyte. Antibodies and cell surface receptors are preferred, with antibodies more preferred. In a preferred embodiment, receptor is generated or selected to be specific for the most unique epitope on the analyte.

Various procedures known in the art may be used for the production of antibodies to analytes of interest. Such antibodies include but are not limited to polyclonal, monoclonal, chimeric, single chain, Fab fragments and an Fab expression library. For the production of antibodies, various host animals may be immunized by injection with a particular analyte or analyte conjugated to an immunogenic carrier, including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to analytes may be prepared by using any technique which provides for the production of antibody molecules by continuous cell lines in culture or in vivo. These include but are not limited to the hybridoma technique originally described by Kohler and Milstein, (*Nature*, 1975, 256:495–497), the more recent human B-cell hybridoma technique (Kosbor et al., 1983, *Immunology Today*, 4:72) and the EBV-hybridoma technique (Cole et al., 1985, *Monoclonal Antibodies and Cancer Therapy*, Alan R. Liss, Inc., pp. 77–96). In an additional embodiment of the invention monoclonal antibodies specific to analytes may be produced in germ-free animals utilizing recent technology (PCT/US90/02545). According to the invention, human antibodies may be used and can be obtained by using human hybridomas (Cote at al., 1983, *Proc. Natl. Acad. Sci.*, 80:2026–2030) or by transforming human B cells with EBV virus in vitro (Cole et al., 1985, in, *Monoclonal Antibodies and Cancer Therapy*, Alan R. Liss, pp. 77–96). In fact, according to the invention, techniques developed for the production of "chimeric antibodies" (Morrison et al., 1984, *Proc. Natl. Acad. Sci.*, 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used; such antibodies are within the scope of this invention.

According to the invention, techniques described for the production of single chain antibodies (U.S. Pat. No. 4,946,778) can be adapted to produce analyte-specific single chain antibodies. An additional embodiment of the invention utilizes the techniques described for the construction of Fab expression libraries (Huse et al., 1989, *Science*, 246:1275–1281) to allow rapid and easy identification of monoclonal Fab fragments with the desired specificity to analytes.

Antibody fragments which contain sites specific for analytes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Alternatively, polyclonal or monoclonal antibody specific for an analyte of interest may be obtained from commercial sources.

Receptor for binding analyte may be purified, e.g., by affinity chromatography or low affinity chromatography. Monoclonal antibody may also be purified by protein A or anti-Ig chromatography. Techniques for purifying polyclonal and monoclonal antibodies are well known in the art. A heterogeneous receptor preparation, such as polyclonal antibody, may also be absorbed with a low concentration (e.g., 1% of the receptor concentration) of ligand to remove any receptors capable of binding ligand with high affinity.

5.1.2. Ligand

As used herein, the term "ligand" includes molecules with limited cross-reactivity with analyte for receptor binding. The term "reland" is used herein interchangably with ligand. Reland is a term coined by the co-inventors hereof to refer to a release ligand. The ligand or reland binds receptor with a low association constant relative to analyte, e.g., preferably less than about 10%, more preferably less than about 1%, and does not affect the stability of an analyte-receptor complex. Ligand comprises an analog of the analyte, including an epitope of the analyte, a derivative of the analyte, a modified analyte, or an isomer of the analyte. Preferably the ligand differs from analyte at or near the receptor binding epitope. These differences may include stearic, configurational, conformational or ionic changes. In another embodiment in which the receptor is a nucleic acid, ligand is a nucleic acid complementary to the "receptor" provided that the degree of complementarity is not as high as the complementarity of the receptor and the nucleic acid analyte.

Analogs of analyte include the analogous molecule from a related species of animal, where such exists, e.g., sheep luteinizing hormone is an analog of human chorionic gonadotropin (see Section 16., infra). Molecules prepared to structurally mimic the analyte are also analogs for use as ligands. Such structural mimics may be, but need not be, of the same chemical nature as the analyte so long as the epitope is chemically similar. Thus, for example, a peptide may be an analog of a protein. A suitable analog will simply share a receptor binding epitope or part of an epitope of the analyte.

Derivatives of analyte may be prepared by adding or deleting functional groups to the molecule. Derivatives may also be natural metabolic products of the analyte. One of ordinary skill will readily know how to prepare or identify derivatives of analytes for use in the invention. Preferably changes in molecular structure of the analyte will alter the receptor binding epitope composition or conformation in order to decrease the binding affinity of receptor for ligand.

Modified analyte includes analyte conjugated to a carrier protein. Addition of bulky groups or ionic groups, such as aliphatic, aromatic or cyclic molecules, to the analyte or to the protein can result in decreased binding affinity for receptor due to stearic and/or charge interference. Alternatively, conjugation with a bulky group may cause a conformational change in the receptor binding site of ligand that decreases binding affinity. Chemical modifications of organic molecules are well known in the art and may be used to modify ligand. In a specific Example, infra, an analyte, norcotinine, modified by the presence of N-isopropyl or N-propyl groups is a preferred ligand in an assay for cotinine.

Isomers of analytes are molecules with the same composition but different configuration. Typically, isomers will have a different configuration at a particular carbon center, e.g., cis versus trans, D versus L. Isomers include diastereomers, which have the opposite configuration at one or more chiral centers, and include enantiomers of analytes. Since biological binding interactions depend on configuration as well as conformation and composition, use of an isomer as ligand can result in much lower binding affinity for receptor.

Where the analyte is a protein, the ligand may be prepared by recombinant DNA methods using site directed or other mutagenesis techniques to alter the amino acid sequence of the protein. These techniques are well known to those skilled in the art (e.g., see Zoller and Smith, 1984, *DNA* 3:479–488; Oliphant et al., 1986, *Gene* 44:177; Hutchinson et al., 1986, *Proc. Nat'l. Acad. Sci. U.S.A.* 83:710). Polymerase chain reaction (PCR) techniques are preferred for site directed mutagenesis (see Higuchi, 1989, "Using PCR to Engineer DNA," in PCR *Technology: Principles and Applications for DNA Amplification*, H. Erlich, ed. Stockton Press, Chapter 6, pp. 61–70).

The ligand may further comprise a carrier protein. The carrier protein may be an essentially inert protein such as albumin or keyhole limpet hemocyanin, but a carrier protein should not be the same carrier used, if any, for immunization to produce antibody to the analyte. An enzyme label may function as a carrier protein.

Ligand may also comprise a linking group. A linking group may space ligand from an enzyme label, thereby preventing or slowing deactivation of the enzyme after a long incubation with receptor. An example of a spacer linking group is ε-aminocaproic acid. Also, bulky linking groups may be used to sterically hinder binding of receptor to ligand. An example of a bulky linking group is p-aminobenzoic acid.

Ligands may be evaluated to show their suitability, for use in a release assay. Ligand evaluation assays include competition assays, binding enhancement assays, direct assays, low affinity chromatography, and microtiter plate release assays, as well as the contemplated release assay itself.

Competitive assays useful for evaluating potential ligands can be run in an ELISA format, but any competitive assay technique may be used. As shown in Example 16., infra, a ligand is much less effective than analyte for inhibiting binding of receptor to solid phase analyte. A molecule that is a poor competitive inhibitor relative to analyte can be a good choice for use as a ligand.

A low concentration of a suitable release ligand may actually appear to enhance binding of receptor to analyte in a competition assay. Thus in a competition type assay with polyclonal antibody, increased absolute signal in the presence of the molecule being tested indicates that molecule may be a suitable release ligand.

When a direct assay is used to evaluate a potential ligand, binding of receptor and ligand is compared to binding of receptor and analyte. An ELISA format is well suited for this type of assay, but other assay formats can also be used. A ligand will demonstrate no more than about 10%, and preferably less than about 1% of the binding activity of analyte. Typically, in an ELISA, binding activity is represented by titer, i.e., dilution or concentration of receptor with a particular binding activity. Alternatively, specific activity at the same receptor concentration can be compared.

If an analyte-specific receptor elutes under mild conditions from an affinity chromatography column prepared with ligand, that ligand may be a useful for a release assay.

In the microtiter plate method, ligand or receptor is coated on the plate. When the microtiter plate is coated with ligand, the ligand will preferably comprise a protein to enhance binding to the plate. The complementary binding partner (receptor or ligand, respectively) is added and a complex allowed to form. If the receptor-ligand pair is suitable, release of receptor or ligand can be detected in a sample supernatant when sample containing analyte is added. As demonstrated in Example 11., infra, a ligand-enzyme conjugate designed for use in a homogeneous assay can be tested in a microtiter plate assay.

5.2. Release Assay Format

The release assay comprising receptor, ligand and a means for detection of released, i.e., dissociated, receptor-ligand complex, has particular utility for analyzing a sample for the presence of a small molecule such as a drug metabolite. Detecting the presence of drugs or drug metabolites in a sample of body fluid from a patient is important for many applications. The presence of drugs or drug metabolites is useful in determining appropriate medical treatment, especially under emergency conditions. Detection of drugs or drug metabolites in a person is important in law enforcement, employment, schools and athletics. Samples may be from any source, but preferably are from an animal, and more preferably from a human. Samples may include but are not limited to be body fluid such as blood, plasma, serum, urine, saliva, bodily exudate, etc.

Analytes may be any antigen, but small analytes (MW of 100 to 1000 Daltons) are of primary interest. Such analytes include therapeutic drugs and metabolites thereof, illicit drugs and metabolites thereof, steroids, and peptide hormones. Nevertheless, release assays for larger molecules such as protein hormones, e.g., insulin, viral antigens, bacterial antigens, serum proteins, antibodies or any antigen of interest where detection of presence (or absence) of the analyte in a rapid, specific, sensitive assay is desirable are also contemplated.

In specific Examples infra, release assays for cotinine (a nicotine metabolite associated with smoking), benzoylecgonine (a cocaine metabolite), tetrahydrocannabinol (the narcotic agent of marijuana), thiazides (a class of diuretics), and beta-blockers are shown. Moreover, it will be apparent that release assays are suitable to detect any analyte of interest.

For example, a release assay may be prepared for HIV antibodies. A format for a release HIV assay follows:

1. Generate antibodies to an HIV peptide modified in such a way as to make it a release ligand, e.g., by substitution of amino acids. This antibody is then analogous to a ligand for purposes of the assay since it is altered relative to the analyte (anti-HIV antibody) of interest.

2. Conjugate the native HIV peptide sequence to a protein such as albumin, and coat the conjugate on plastic beads or wells of microtiter plates. The peptide-protein conjugate acts as the receptor for analyte for purposes of this assay.

3. Mix the receptor (conjugate) and the ligand (antibody) so that complex is formed. The ligand should be labeled with a marker e.g., a fluorescent tag. Wash the plate after complex forms.

4. Add sample containing analyte (anti-HIV antibodies) to the solid phase. The anti-HIV antibodies displace the labeled antibody. Measure the amount of released label.

Preferably the ligand antibody for an HIV assay is a monoclonal antibody.

The present invention provides for positively detecting dissociation of a receptor-ligand complex resulting in release of the labeled component. Positive detection means that signal positively correlates with the amount of analyte in a sample. A positive correlation is advantageous because it is psychologically satisfying that presence of signal or increase in signal intensity indicates presence of analyte in a sample. Results obtained by assay methods in which detection of signal decreases when analyte is present are susceptible to misinterpretation. It is desirable to employ an assay, such as that of the present invention, in which only a positive result generates signal. Assays of the invention are equally suitable for use both in a laboratory by technical personnel as well as outside a laboratory by both technical and non-technical personnel.

Accordingly, the invention provides for detecting release of a component of a receptor-ligand complex. In a heterogeneous release assay (Section 5.2.2, infra), either receptor or ligand may be labeled so that upon release in the presence of analyte, the label signal is separated from reaction products and is detected. In a homogeneous release assay (Section 5.2.1, infra), it is preferable to label ligand, but under certain circumstances, when using a nonenzymatic label, receptor can be labeled. For example, when a fluorescent label is used, ligand may contain a fluorescence quencher. In the receptor-ligand complex, the fluorescent signal is quenched, and there is no detection of fluorescence until dissociation occurs in the presence of analyte. Suitable labels include enzymes, fluorophores, chromophores, latex particles, colloidal gold, dyes and chemiluminescent agents.

The means for detecting dissociation of a receptor-ligand complex depends in part on whether the assay is homogeneous or heterogeneous, as described below in sections 5.2.1. and 5.2.2.

Once suitable binding receptor, release ligand, and means for detecting a particular analyte are chosen, the assay system must be optimized for use with a particular sample matrix. A urine sample will have different intrinsic characteristics than a sample in aqueous buffer. The same is true for sample from saliva, blood, plasma or serum, or any body fluid. The assay may be optimized by varying reagent concentration, buffer composition, release time, detection time, baseline controls, and other variables. These variables are well known in the art, and it will be readily understood how to adjust them for optimum assay specificity and sensitivity with a particular assay matrix.

5.2.1. Homogeneous Release Assays

The release assay may be performed homogeneous liquid phase. Such an assay is preferred because it can be performed in a single reaction vessel, and thus is well suited for use in automated analyzers.

In one embodiment, the ligand may be conjugated to an enzyme label that retains a detectable level of enzyme activity. A ligand-enzyme conjugate is selected such that upon binding of receptor to ligand, enzyme activity decreases. To increase sensitivity, preferably one receptor binding site is present on the enzyme, but more than one is also acceptable.

When analyte is added to the receptor-ligand complex, the complex dissociates into its receptor and ligand components and released receptor binds analyte upon release of the ligand-enzyme conjugate, enzyme catalytic activity increases. This increase is detected by measuring the rate of product formation. Any enzyme-substrate system can be used, with the proviso that no endogenous enzyme present in sample will artificially increase the rate of product formation. Preferably the enzyme is glucose-6-phosphate dehydrogenase, and the reaction product is reduced nicotine-adenine dinucleotide (NADH), which can be detected by absorbance at 340 nm.

Alternatively, a receptor-ligand complex in a homogeneous release assay may comprise a fluorescent label or chemiluminescent label attached to ligand and a fluorescence quencher attached to the receptor. The receptor may itself quench fluorescence. In the complex, the fluorescence or luminescence will be quenched and no signal will be observed. However, upon dissociation of the receptor-ligand complex and release of receptor and ligand in the presence of analyte, quenching will diminish, and signal will be observed. Other proximity dependent signal attenuators, such as fluorescence polarization, are known in the art, and can be adapted for use in a release assay. It will further be appreciated that the label may be on receptor and the quencher on ligand.

5.2.2. Heterogeneous Release Assays

In another embodiment, a heterogeneous solid-phase/liquid-phase release assay is provided. In such an assay, either receptor or ligand is irreversibly absorbed to a solid phase support. As used herein, the term "irreversibly absorbed" includes covalent, non-covalent and ionic association. Solid phase supports include plastic, polymer beads, glass beads, glass, silica gel, and membranes. In Examples infra, solid phase supports are plastic microtiter plate wells and nitrocellulose membranes. However, the release assay is not limited to a particular choice of solid phase support and any solid phase support known in the art may be used.

The binding partner of the receptor or ligand absorbed to the solid phase support, i.e., the ligand or receptor respectively, is labeled, and a stable complex comprising the labeled element and the solid phase element is formed. Once a stable receptor-ligand complex is formed, it can be exposed to sample. If the analyte of interest is present in the sample, the release reaction occurs and signal from the label is detected in the liquid phase. The extent of release, and thus the signal intensity in the liquid phase, positively correlates with the amount of analyte in the sample. The signal intensity in the solid phase decreases inversely with the amount of analyte in the sample (see Table 6).

Many labels can be used in the heterogeneous release assay. Enzyme labels are practical, even for a single vessel assay, because enzymes bound to a solid phase can have 10-to 20-fold less catalytic activity than the same enzyme in solution. Moreover, as with homogeneous release, binding of receptor to ligand-enzyme conjugate may reduce enzyme activity. Other labels such as chromophores, fluorophores, chemiluminescent agents, radioisotopes, chelating complexes, dyes, colloidal gold and latex particles can be detected in the liquid phase after release reaction as increased optical density, fluorescence, luminescence, radioactivity, color (for dyes), and turbidity (for colloidal gold and latex particles), respectively. Where the signal from label that remains bound in the receptor-ligand complex cannot be detected, the assay may be performed in a single vessel.

In a particular embodiment preferred for non-laboratory settings, the presence of an analyte is indicated by the appearance of a shape, i.e., a letter, in a reaction field on a solid phase support. Accordingly, a reaction field comprising an indicator zone and a control zone is prepared on a solid phase support. The indicator zone comprises either immobilized receptor or ligand, as provided by the heterogeneous assay format. A receptor-ligand complex in the indicator zone is sensitive to the release reaction. The control zone comprises a different receptor-ligand complex. The receptor-ligand complex in the control zone is not susceptible to the specific release reaction, but will indicate non-specific release if conditions are such as to cause nonspecific release.

In practice, contacting sample containing the analyte of interest to the reaction field will result in a detectable release reaction in the indicator zone, and no reaction in the control zone. The release reaction is detected as formation of a contrasting zone corresponding to the indicator zone. To accomplish this, label for both the release complex and the control complex is chosen to contrast with the solid support.

If there is no development of a contrast zone, the sample is negative. "Fade" of both the indicator zone and control zone, i.e., release of label from both complexes, indicates a false positive reaction, inappropriate reaction conditions, and possible adulteration of the sample. In this way, the control zone provides a control for accurate assay results.

Preferably different letters or symbols are used as the indicator depending on the analyte of interest. For example, indicator zone specific for cocaine use may be shaped like the letter "c"; an indicator zone for marijuana use shaped like the letter "M" (or "T" for tetrahydrocannabinol), and a zone to indicate nicotine use shaped like the letter "N".

The control zone comprising a complex immobilized control receptor or ligand and labeled ligand or receptor, respectively, is analogous to the indicator zone, with the proviso that the control complex in insensitive to the presence of analyte, while the complex in the indicator zone is released in the presence of analyte. For example, if the analyte of interest is cotinine, the immobilized ligand is cotinine coupled to bovine gamma globulin via an aminocaproic acid linker, and the receptor is anti-carboxy-cotinine labeled with blue latex, a suitable control ligand is immobilized trinitrophenol (TNP) conjugated to bovine serum albumin, and a suitable control receptor is anti-TNP antibody, also labeled with blue latex. In the presence of cotinine, labeled anti-carboxycotinine would be released and a contrasting zone develop. The TNP-anti-TNP complex is unaffected by cotinine.

It is clear that other receptor ligand combinations will work equally well as control complexes. For example, in an assay to detect cotinine, a control complex could be immobilized ecgonine-anti-benzoylecgonine. It is further envisioned that a single solid phase support can contain more than one detection field, since each detection field is specific for a particular analyte and insensitive for any other analyte. Thus, the invention provides an assay for multiple analytes, e.g., tetrahydrocannabinol, benzoylecgonine, and cotinine, in a single format.

Suitable labels for use in this assay include but are not limited to colored latex particles, dyes, colloidal gold, and enzymes that catalyze production of an insoluble colored reaction product when a white or light colored solid phase support is used, and white latex when a dark solid please support is used. Preferably, colored latex particles are used as labels. Also, any solid phase support can be used in this embodiment, but plastic and membranes are preferred.

In a preferred embodiment, such as described in Section 15., infra, the solid phase support comprising receptor-ligand complex and control complex is provided dry.

The invention will be further clarified by the following Examples, which are intended to be purely exemplary of the invention and not as limitations of the invention. Indeed, various modifications of the invention in addition to those shown and described herein will become apparent to those skilled in the art from the description and accompanying drawings. Such modifications are intended to fall within the scope of the appended claims.

6. EXAMPLE: SOLID PHASE RELEASE ASSAY FOR COTININE

Cotinine and trans-3'-hydroxycotinine are the major metabolites of nicotine (Langone et al., 1973, *Biochem.* 12:5025–30; Jacob et al., 1991, *J. Chromatography* 222:61–70; Neurath et al., 1987, *Int. Arch. Occup. Environ. Health* 59:199–201). They appear in urine in a 1:3 ratio (Newrath et al., supra). The detection of cotinine in urine, serum or saliva is the most commonly used biochemical method to determine levels of exposure to nicotine (Fitzpatrick, 1991, *C.N.N.* 11). Unlike other drugs of abuse, cotinine is found in bodily fluids of non users due to passive smoking. The range of interest for a cotinine assay is from 0.010 µg/ml necessary for saliva and blood testing, to <10µg/ml for urine of tobacco users (Greenberg et al., 1984, *N. Engl. J. Med.* 310:1075–78; Matsukura et al., 1984, *N. Engl. J.Med.* 311:828–31; Sepkovicet al., 1985, *Am. J. Public Health* 75:663–6; Sepkovic et al., 1986, *J.A.M.A.* 256:863; Jarvis et al., 1987, *Am. J. Public Health*

77:1435–8; Schepers and Walk, 1988, *Arch. Toxicol.* 62:395–7; Langone et al., 1988, *J.I.M.* 114:73–8).

This example reports the use of three different cotinine ligands in a heterogeneous solid phase release assay. One ligand comprises a cotinine metabolite directly bound to an inert carrier protein (hydroxy-cotinine-BGG), another ligand comprises the cotinine metabolite conjugated to the protein via a bulky linker (hydroxycotinine-aminobenzyl-BGG) and a third comprises the cotinine metabolite conjugated to the protein via a spacer linker (hydroxycotinine-aminocaproyl-BGG).

6.1. Materials and Methods

Trans-3'-hydroxycotinine was obtained according to a published method (Jacob et al., 1990, J. Med. Chem. 33:1888). Succinic anhydride and dimethyl-formamide (DMF) were obtained from Aldrich Chemical Co. Pyridine, N-hydroxysuccinimide, 1-ethyl-3-(3-dimethylaminopropyl) carbodiiumide (EDC), p-aminobenzoic acid (PABA), $\epsilon$-aminocaproic acid (ACA) and bovine gamma globulin (BGG) were obtained from Sigma.

6.1.1. Preparation of Hydroxycotinine-BGG Ligand

Step A. Hydroxycotinine hemisuccinate was prepared as follows. In a glass tube, 19 mg of trans-3'-hydroxycotinine were dissolved in 1 ml of DMF. In this solution 21 mg of succinic anhydride were dissolved. After adding 20 µl of pyridine, the tube was covered (PARAFILM®) and incubated overnight at 37° C.

Step B. After equilibration at room temperature (r.t.), 14 mg of N-hydroxysuccinimide and 23 mg of EDC were dissolved in the cotinine solution. The solution was covered (parafilm) and incubated 3 hours at room temperature to activate the cotinine hemisuccinate.

Step C. Activated cotinine hemisuccinate (400 µl of the solution from step B.) was added to the solution of 6 mg BGG dissolved in 1 ml of PBS. The mixture was gently mixed and incubated 1 hour at room temperature, then overnight at 4° C. The resulting conjugate was dialyzed against 6 changes of PBS for 48 hours.

6.1.2. Preparation of Hydroxycotinine-aminobenzoyl-BGG Ligand

Step D. In 0.6 ml of PBS were dissolved 6 mg of PABA. To this solution were added 400 µl of activated cotinine hemisuccinate prepared according to step B., supra. The resulting solution was mixed well and incubated for 1 hour at room temperature and overnight at 4° C.

Step E. The hydroxycotinine-hemisuccinate-PABA was brought to room temperature and activated by addition of 0.5 ml of 14 mg/ml N-hydroxysuccinimide in DMF and 0.5 ml of 24 mg/ml EDC in DMF. The mixture was incubated 3 hours at room temperature. To 6 mg of BGG in 2 ml of PBS were added 400 µl of activated cotinine-PABA. The resulting solution was mixed gently and incubated 1 hour at room temperature and overnight at 4° C. The resulting conjugate was dialyzed against 6 changes of PBS over 48 hours.

6.1.3. Preparation of Hydroxycotinine-Aminocaproyl-BGG Ligand

Step F. To a solution of 4 mg ACA in 0.6 ml of PBS were added 400 µl of the activated cotinine succinate solution prepared according to step B., supra. The resulting solution was mixed very well and incubated 1 hour at room temperature and overnight at 4° C.

Step G. The hydroxycotininehemisuccinate-ACA solution was brought to room temperature and activated by addition of 0.5 ml of 14 mg/ml N-hydroxysuccinimide in DMF and 0.5 ml of 24 mg/ml EDC in DMF. The resulting mixture was incubated for 3 hours at room temperature. To 6 mg of BGG in 2 ml of PBS were added 400 µl of activated cotinine-ACA. The resulting solution was mixed gently and incubated at room temperature for 1 hour, then overnight at 4° C. The resulting conjugate was dialyzed against six changes of PBS over 48 hours.

6.1.4. Antiserum Binding Reagent

Antiserum to carboxycotinine was obtained as follows: 320 mg of keyhole limpet hemocyanin (KLH) protein (Sigma) were dissolved in 40 ml of deionized water. To this were added 300 mg of trans-4'-carboxycotinine (Aldrich) with mixing until it was dissolved. Then 300 mg of EDC were added to the reaction mixture with stirring, which was continued overnight at room temperature. The KLH-carboxycotinine conjugate was dialyzed for 8 hours at 2°–8° against phosphate buffered saline. The dialysis fluid was changed once after 4 hours.

Rabbits were immunized with the immunogen in Freund's adjuvant, with multiple injections over several months according to standard protocols. Test bleedings were made at defined intervals, and increases in antibody titer measured using an enzyme immunoassay for cotinine. Measurements of antibody affinity and cross-reactivity were also performed. When these assays indicated satisfactory antibody performance, rabbits were bled and sera were isolated and pooled. Antiserum was stored at –40° C.

The IgG fraction was separated from serum by ammonium sulfate precipitation. An immunoaffinity chromatography column was prepared by coupling succinylated hydroxycotinine through its carboxyl group to aminosepharose 4B (see section 9., infra). The affinity purified antibody was labeled with horseradish peroxidase using the sodium-m-periodate method.

Antisera prepared against 4'-carboxycotinine, which is conjugated to carrier protein at the 4' position, were expected to bind cotinine conjugated to protein at the 3' position with lower affinity.

6.1.5. Assay

Microtiter plates were coated overnight with 100 µl of each ligand at 1 µg protein per ml of PBS. Dried plates were incubated for 1 hr with 100 µl of enzyme-labeled antibody. Excess antibody was washed out and 90 µl of distilled water and 10 µl of urine sample or standard were added to each well. After 2 minutes of shaking, the supernatant was transferred to uncoated wells. Released label in the supernatant was quantitated after reaction with TMB substrate for 15 minutes by measurement of O.D. at 450 nm.

6.2. Results

Release of labeled antibody complexed to solid phase ligand was detected in supernatant when free cotinine was present in sample. A comparison of release from solid phase hydroxycotinine-PABA-BGG and solid phase hydroxycotinine-ACA-BGG indicates that after 2 minutes of exposure free cotinine induces the release of anti-cotinine antibody bound to both antigens in a concentration dependent manner (FIG. 1). The results indicate that release from hydroxycotinine-ACA-BGG is slightly more efficient.

Enhanced release reactions were observed for release when the release portion of the assay is extended to 10 minutes (FIG. 2). Increases in could be observed at as low as 0.5 µg/ml cotinine. Again, release from hydroxycotinine- ACA-BGG was more efficient. A comparison of release after 2 minutes of incubation with sample in urine and synthetic matrices (FIG. 3) indicates that (i) assay sensitivity is greater in synthetic matrix than in urine matrix; and (ii) that hydroxycotinine-ACA-BGG acts more efficiently for release of anti-cotinine antibody.

6.3. Discussion

These results show that a release assay indicates the presence of free cotinine in a sample of urine or all artificial urine matrix. Assay plates prepared by coating the microwells with cotinine ligand conjugated at the 3' position to a protein and forming a complex with antibody specific for cotinine conjugated to the immunogenic carrier protein at the 4' position, the detection of free cotinine in sample can be completed using this assay in under 30 minutes. Comparison of FIGS. 2 and 3 shows that release can be observed as soon as 2 minutes after sample is added.

Subtle differences in binding affinity affect the sensitivity of a release assay. Release from the hydroxycotinine-aminocaproic acid-bovine gamma globulin ligand gave slightly more sensitive readings than release from hydroxycotinine-aminobenzoyl-BGG. These results demonstrate how exploitation of differences in binding affinity allows development of sensitive immunoassays.

7. EXAMPLE: MICROTITER PLATE METHOD OF ASSAYING LIGAND-PROTEIN CONJUGATES

A solid phase assay provides a method to compare ligand-protein conjugate preparations for use in release assays, and to determine whether a particular ligand binds analyte-specific antibody with sufficiently low affinity. The present example reports results with a cotinine ligand.

7.1. Materials and Methods

Reagents, hydroxycotinine-p-amino-benzoic acid-bovine gamma globulin (BGG) and hydroxycotinine-ε-aminoncaproic acid-BGG were prepared as described in section 6.1., supra.

7.1.1. Assay Protocol

Microtiter plates were coated with cotinine-ligand as described in Section 6.1.5., supra. The wells were washed twice with wash buffer and 100 μl of anti-cotinine-peroxidase conjugate (Section 6.1.4., supra) were added to each well. The plate was incubated 60 min at r.t. and washed twice with wash buffer. To each well were added 100 μl of wash buffer and 10 μl of sample. Samples consisted of 0, 0.5, 2.0 and 10 μg/ml cotinine in urine, and two negative and two positive urine samples. The plate was incubated 10 minutes at r.t. with shaking, and 100 μl of supernatant were removed and transferred to replicate wells of an uncoated microtiter plate. To the wells containing supernatant were added 100 μl of 2× TMB substrate solution. The plate was incubated 3 min at r.t., and then the reaction stopped by addition of 50 μl 2 N sulfuric acid to each well. Absorbance at 450 nm was measured.

7.2. Results

Presence of cotinine in sample caused release of labeled anti-cotinine antibody from the cotinine-ligand solid phase. The $A_{450}$ value of supernatant correlated positively with the amount of free cotinine present in cotinine-spiked urine samples. Furthermore, the results with negative and positive urine samples demonstrate the usefulness of the assay to detect cotinine in urine. The results are summarized in Table 1.

TABLE 1

COTININE-INDUCED RELEASE FROM COTININE-BGG-CONJUGATES.

| COTININE CONC (μg/ml) | $A_{450}$ COTININE-PABA-BGG | COTININE-ACA-BGG |
|---|---|---|
| 0 | 0.637 | 0.589 |
| 0.5 | 0.658 | 0.721 |
| 2.0 | 0.946 | 0.986 |
| 10.0 | 2.247 | 2.251 |
| NEG. URINE 1 | 0.515 | 0.585 |
| NEG. URINE 2 | 0.368 | 0.420 |
| POS. URINE 1 | 1.161 | 1.269 |
| POS. URINE 2 | 1.077 | 1.198 |

7.3. DISCUSSION

These results show that a microtiter plate assay provides a convenient support for demonstrating the usefulness of a particular ligand-protein conjugate for a release assay. In this assay use of a bulky or spacer linkers in the ligand made little difference in the results.

8. EXAMPLE: HOMOGENEOUS RELEASE ASSAY FOR COTININE

The release system provides improved sensitivity and specificity over previous assays by taking advantage of the specificity of dissociation reactions. Dissociation reactions offer the advantage that they are less subject to interfering substances.

The present example demonstrates (1) preparation of cotinine ligands labeled with the enzyme glucose-6-phosphate dehydrogenase; (2) inhibition of enzymatic-activity of the enzymecotinine conjugate in the presence of anti-cotinine; (3) displacement of anti-cotinine from the enzymecotinine conjugate in the presence of cotinine; (4) an automated assay for release of antibody from ligand, particularly after to 22 hrs of complex incubation; and (5) stabilization of an antibody-ligand complex for up to 6 days.

8.1. Materials and Methods

The following reagents were used: trans-4-carboxycotinine, N-hydroxysuccinimide, 1,3-dicyclocarbodiimide, and dimethylformamide (DMF), all from Aldrich Chemical Co.; glucose-6-phosphate dehydrogenase (Beckman, 367 IU/mg protein); glucose-6-phosphate and beta-nicotinamide adenine dinucleotide reduced form (NAD), both from Sigma Chemical Co.; and carbinol [2-(2-ethoxyethoxy)ethanol, from Aldrich Chemical Cu.

Preparation of cis-hydroxycotinine-glucose-6-phosphate dehydrogenase is described in Section 10.1.3., infra.

8.1.1. Assay Procedure

Assay buffer was 0.05 M Tris-HCl, pH 7.8, equilibrated at 3° C. To 150 μl of assay buffer were added 10 μl of cotinine-enzyme conjugate and 1 μl of anti-cotinine antibody (Section 6.1.4., supra), and the solution incubated 10 minutes at 37° C. To this solution were added 10 μl of sample containing cotinine. The reaction was started by addition of 20 μl of glucose-6-phosphate/NAD, and absorbance at 340 nm read every 1 minute.

A control reaction in the absence of antibody was prepared by adding 10 μl of enzyme-cotinine conjugate to 160 μl of assay buffer, and equilibrating at 37° C. for 10 min. To start the reaction, 20 μl of glucose-6-phosphate/NAD were added, and $A_{340}$ was measured at intervals of 1 minute.

Cotinine-enzyme conjugate was prepared at 1 mg/ml of protein and diluted 500-fold to a final concentration of 2.0 μg/ml. The anti-cotinine antibody was present in stock solution at an approximate concentration of 15 mg/ml. The glucose-6-phosphate-NAD solution was prepared by mixing 3 volumes of 0.11M glucose-6-phosphate with 2 volumes of 0.1M NAD.

8.1.2. Automated Assay Procedure

Reagent A was prepared with an anti-cotinine anti-serum (1:150 dilution), cotinine-glucose-6-phosphate dehydrogenase conjugate, and 0.0015% Kathon CG in 0.05M Tris-HCl, 0.005M $MgCl_2$, pH 7.8. Reagent B contained 6.2 mg/ml glucose-6-phosphate and 13.3 mg/ml NAD.

Reagent reservoirs on an EPOS automated analyzer (Eppendorf) were filled with reagents A and B. Reagents A (0.2 ml) was incubated for 0, 18 or 22 hrs prior to addition of sample (0.01 ml). Samples, including standards, were pipetted into the mixture of reagents A. Reagent B (0.05 ml) was added, and absorbance at $340_{nm}$, was measured at 0 and 5 min.

8.2. Results 8.2.1. Reduction and Inhibition of Enzyme Activity

Enzyme activity of cis-hydroxycotinine-enzyme conjugate was assayed in the presence and absence of anti-cotinine antibody. The results are summarized in FIGS. 5 and 6.

Conjugation of cotinine to enzyme results in decreased enzyme activity. Addition of anti-cotinine antibody to the enzyme-cotinine conjugate further reduced (inhibited) enzyme activity (FIG. 4). Inhibition of enzyme activity by antibody binding is completely reversed by the addition of 10 μl sample of 4 μg/ml cotinine (FIG. 5).

8.2.2. Automated Enzyme Assay

Samples spiked with known amounts of cotinine, or which were known to be positive for cotinine, were assayed 0, 18 and 22 hrs after mixing the antibody/ligand-enzyme conjugate. The assay was performed as described in Section 8.1.2. The results indicate that although long incubation times result in somewhat decreased absolute rate of change, presence of cotinine in the sample could be detected at even the lowest concentration. These results are shown in Table 2.

TABLE 2

AUTOMATED COTININE RELEASE ASSAY.

| COTININE CONC. | OD Rate Change (mAU per min) TIME OF PREINCUBATION OF REAGENT A PRIOR TO ADDITION OF STANDARDS OR SAMPLES | | |
|---|---|---|---|
| μg/ml | 0 HOURS | 18 HOURS | 22 HOURS |
| 0 | 102.1 | 101.1 | 102.4 |
| 0.5 | 116.3 | 108.5 | 109.1 |
| 1.0 | 123.0 | 111.0 | 111.3 |
| 2.0 | 127.3 | 114.5 | 114.8 |
| 4.0 | 132.5 | 118.2 | 118.2 |
| 8.0 | 138.0 | 121.8 | 121.7 |
| POSITIVE #1 | 131.8 | 118.5 | 117.7 |
| POSITIVE #2 | 130.0 | 117.7 | 117.9 |
| POSITIVE #3 | 110.6 | 105.7 | 104.6 |
| NEGATIVE #1 (T.D.) | 103.0 | 104.7 | 101.2 |

These data indicate that the mixed reagent A remains stable for as long as 22 hours; A statistical analysis of the estimated amount of cotinine in the positive and negative urine samples bears out this conclusion (Table 3).

TABLE 3

STATISTICAL ANALYSIS OF DATA FROM THE AUTOMATED ASSAY.

| REAGENTS A PRE-INCUBATION TIME | STANDARD CURVES | | ESTIMATED CONCENTRATION OF COTININE IN SAMPLES (μg/ml) | | | |
|---|---|---|---|---|---|---|
| | SLOPE | INTERCEPT | #1 | #2 | #3 | T.D.* |
| ZERO TIME | 0.9939 | 0.00838 | 3.55 | 2.80 | 0.221 | 0.08 |
| 18 HOURS | 1.0583 | −0.127 | 4.27 | 3.63 | 0.309 | 0.25 |
| 22 HOURS | 1.0649 | −0.142 | 3.57 | 3.72 | 0.211 | 0.101 |

*Negative sample.

Table 3 shows that after 0, 18, or 22 hours of preincubation, agreement as to the amount of cotinine present in a sample is reasonably good. For example, the estimated concentration of cotinine in positive sample #1 ranges between 3.6 and 4.3 μg/ml. Similar data are obtained for all four samples. Thus although the absolute absorbance change is greater after <1 hours of incubation time, all three curves provide good data for estimating concentration by extrapolation from the standard curve (FIG. 6).

8.2.3. Stabilization of a Receptor-Ligand Complex in High Salt Solution

Antibody-ligand complex was formed in 0.5M Tris-HCl, pH 7.9, containing 3 mM magnesium chloride and 0 or 5% sodium chloride. The assay was run using the format described in Section 8.1.1. The homogeneous release assay for cotinine was tested for receptor-ligand complex stability for up to six days. Results are shown in Table 4.

TABLE 4

RELEASE ASSAY AFTER LONG TERM INCUBATION OF AN ANTIBODY-LIGAND COMPLEX.

| Cotinine conc. (μg/ml) | | Rate of OD Change (mAU/min) | |
|---|---|---|---|
| | | 0% NACL | 5% NACL |
| 0 | Day 0 | 12.09 | 16.6 |
| 0.5 | | 13.15 | 17.63 |
| 1 | | 13.43 | 18.96 |
| 2 | | 13.85 | 18.3 |
| Delta* | | 1.76 | 1.7 |
| 0 | Day 1 | 7.02 | 9.67 |

TABLE 4-continued

RELEASE ASSAY AFTER LONG TERM INCUBATION
OF AN ANTIBODY-LIGAND COMPLEX.

| Cotinine conc. | | Rate of OD Change (mAU/min) | |
|---|---|---|---|
| (µg/ml) | | 0% NACL | 5% NACL |
| 0.5 | | 7.5 | 10 |
| 1 | | 7.7 | 11 |
| 2 | | 7.8 | 11 |
| Delta* | | 0.78 | 1.33 |
| 0 | Day 6 | 7.3 | 9.1 |
| 0.5 | | 7.8 | 9.3 |
| 1 | | 7.6 | 9.6 |
| 2 | | 7.9 | 10.7 |
| Delta* | | 0.6 | 1.6 |

*Delta is the enzyme activity in the presence of 2 µg/ml cotinine with the baseline (activity in the absence of cotinine) subtracted.

The data show that 5% sodium chloride stabilized both enzyme activity and the antibody-ligand complex in releasable form. Although the magnitude of the maximum enzyme activity decreased with time even in the presence of NaCl from 18.3 (day 0), to 11 (day 1), to 10.7 (day 6), the enzyme activity with baseline subtracted remains fairly constant at 1.7, 1.33 and 1.6 for days 0, 1 and 6, respectively. The samples incubated in the absence of NaCl did not remain stable.

9. EXAMPLE: PREPARATION OF LOW AFFINITY ANTIBODIES FOR USE IN RELEASE ASSAYS

Low affinity chromatography provides a useful method to purify antibodies or other receptors, and may also indicate suitable ligands. In particular, receptor elution under mild conditions results in much higher yields than conventional affinity chromatography, e.g., close to 100%. The mild conditions preserve antibody from irreversible denaturation and extend the column life. An affinity column prepared with a potential ligand indicates that the ligand can be used in a release assay with that receptor. This Example demonstrates purification of anti-cotinine antibodies by a ligand, trans-3-hydroxycotinine, affinity column.

9.1. Materials and Methods

9.1.1. Preparation of Immunoabsorbent

Cotinine hemisuccinate was prepared by dissolving 19 mg of trans-3'-hydroxycotinine in 1 ml of dimethylformamide (Aldrich). 21 mg of succinic anhydride (Aldrich) were added, followed by 15 µl of pyridine (Aldrich). The mixture was incubated overnight at 45° C.

Iminodipropylamine-Sepharose was prepared as followed. Cyanogen bromide (CNBr) activated Sepharose 4B (Sigma), 1 gm, was hydrated and washed several times with 0.1M carbonate buffer, pH 9.5. Three ml of 0.1M 3,3'-iminobispropylamine (Sigma) were added to 3 ml of CNBr-Sepharose gel and the mixture mixed overnight at room temperature. The amino Sepharose was washed with a buffer consisting of 0.1M sodium carbonate, pH 8.5, 0.1M sodium bicarbonate, pH 8.5, and 0.5M sodium chloride until no reactivity with trinitrobenzene-sulfonic acid with free amino groups was detected.

Hydroxycotinine hemisuccinate succinic ester was prepared by adding to 1 ml of cotinine hemisuccinate 14 mg of N-hydroxysuccinimide (Sigma) and 23 mg of 1-ethyl-3-(dimethylaminopropyl) carbodiimide (Sigma) and incubating at room temperature for 3 ]]ours.

Hydroxycotinine-Sepharose was prepared by mixing 0.45 ml of hydroxycotinine-succinyl ester with 1 ml of iminodipropylaminosepharose and 0.6ml of 0.2M sodium bicarbonate. The mixture was gently shaken for 3 hours at room temperature and kept at 4° C. overnight.

9.1.2. Affinity Chromatography

A small column was packed with the hydroxycotinine-Sepharose gel, and the column washed 3 times with 1 ml of 0.5M sodium chloride, and then with phosphate buffered saline (PBS).

A portion of anti-cotinine antiserum produced by injecting rabbits with carboxycotinine (section 6.1.4., supra) was diluted 1:1 with PBS, and the whole mixture (2.1 ml) applied to the column. The material was allowed to equilibrate for 10 minutes, and then the column was eluted sequentially with PBS, 0.1M acetate buffer, pH 4.0, and 0.1M citrate buffer, pH 2.3. The column was then washed with 1M sodium chloride followed by PBS. Protein concentration was determined on fractions using Pierce Coomassie blue reagent, and antibody activity by determining reactivity on plates coated with cotinine in an ELISA assay. Orthophenylenediamine (OPD) and peroxide were used as indicator and substrate respectively for peroxidase.

9.2. Results

Although most protein eluted in early fractions (void volume) from the affinity column, antibody activity was found in later fractions. Fraction 14 contains antibodies with high affinity for cotinine. The antibody yield was greater than 80%, which is very high. Furthermore, the specific activity of the low affinity purified antibody as demonstrated by the number of tests performed was better than with whole sera or the IgG fraction thereof (data not shown).

9.3. Discussion

Low affinity chromatography provides a superior way to obtain low affinity antibodies for use in release assays with that ligand. Low affinity antibodies elute from an immunoaffinity chromatography column earlier, under gentler conditions, than high affinity antibodies. Less stringent conditions are sufficient to elute low affinity antibodies from a solid phase chromatographic support only if the antibody-ligand interaction is itself of sufficiently low affinity.

Elution under neutral or mild conditions provides the additional benefit of reducing or preventing antibody denaturation.

10. PREPARATION OF LOW AFFINITY ANALOGS OF COTININE AND THEIR EFFICACY IN A RELEASE ASSAY

Ligands can be prepared by using analogs or stereoisomers of analogs of the analyte, thus introducing a configurational or constitutional difference that can result in lower affinity binding to analyte-specific antibody.

In the present example, anti-cotinine antibody prepared from rabbits immunized with carboxycotinine conjugated to KLH (see Section 6.1.4., supra) is shown to have useful release properties from trans-3'-hydroxy-cotinine conjugates of horseradish peroxidase in the presence of free cotinine. The optical isomer of trans-3'-hydroxycotinine is cis-3'-hydroxycotinine, and this is also shown to be a superior ligand.

10.1. MATERIALS AND METHODS

10.1.1. Extensive Modification of Glucose-6-Phosphate Dehydrogenase with Trans-3'-Hydroxycotinine to Form a Ligand Eleven mg of trans-3'-hydroxycotinine were dissolved in 0.29 ml of dimethylformamide; 12 mg of succinic anhydride were added to the mixture. When all solids had dissolved, 9 µl of pyridine were added, and the tube was capped tightly and incubated at 37° C. overnight. To the hydroxycotinine succinate mixture were added 7 mg of N-hydroxysuccinimide and 12 mg of N,N'-dicyclohexylcarbodiimide. This mixture was incubated for 2 hours at room temperature.

Three tubes were prepared, each containing 1 ml of 0.1M carbonate buffer, pH 9.0 and 2.8 mg glucose-6-phosphate dehydrogenase. To the first tube were added 35 µl of the activated transhydroxycotinine over a period of 1 hour, in aliquots of 5 µl at 10 minute intervals. This preparation was designated as RL-24. To the second tube were added 70 µl of activated trans-hydroxycotinine, in the same regimen as above. This preparation was designated as RL-25. To the third tube were added 105 µl of activated trans-hydroxycotinine, in the same regimen as above, in 15 µl aliquots. This preparation was designated as RL-26.

Fifteen minutes after the last addition of activated transhydroxycotinine, samples were transferred to dialysis bags and dialyzed at 2°–8° C. against 0.05M Tris buffer, pH 7.8. Dialysis was continued for approximately 44 hours with several changes of fluid.

10.1.2. Less Extensive Modification of Glucose-6-Phosphate Dehydrogenase with Transhydroxycotinine to Form of Ligand 9.5 mg of trans-3'-hydroxycotinine were dissolved in 0.25 ml of dimethylformamide. Then 6 mg of succinic anhydride were added to the mixture and mixed until dissolved. 7.5 µl of pyridine were added, and the tube was capped tightly and incubated at 37° C. overnight.

To this mixture were added 6 mg of N-hydroxysuccinimide and 10 mg of N,N'dicyclohexylcarbodiimide. The mixture was incubated for 45 min at room temperature with stirring.

Two tubes were prepared, each containing 1 ml of 0.1M carbonate buffer, pH 9.0, and 2.8 mg glucose-6-phosphate dehydrogenase. To the first tube were added 25 µl of the activated transhydroxycotinine over a period of 1 hour, in aliquots of 5 µl at 10 minute intervals. This preparation was designated as RL-29. To the second tube were added 70 µl of activated trans-hydroxycotinine in the same regimen as above, in 10 µl aliquots. This preparation was designated as RL-30.

The preparations were dialyzed overnight in the cold against 0.05M Tris buffer, pH 7.8.

10.1.3. A CIS-3'-HYDROXYCOTININE LIGAND 47.5 mg of cis-3'-hydroxycotinine were dissolved in 0.4 ml of pyridine. To this solution were added 10 mg of succinic anhydride and the mixture stirred until dissolved. The mixture was incubated overnight at 37° C. and then held at room temperature.

Cis-hydroxycotinine hemisuccinate was separated from the reaction mixture with preparative thin layer chromatography on silica gel using a solvent system composed of benzene:methanol:ammonium hydroxide, 10:3:0.5. The cis-hydroxycotinine was visualized with a UV lamp. The desired product was isolated as follows: the area on the chromatogram containing the cis-hydroxycotinine hemisuccinate was scraped off and placed in a tube. One ml of methanol was added and the tube shaken by hand while the contents were mixed with a glass spatula. The tube was centrifuged briefly at 1500 rpm. The supernatant was collected, and the silica gel washed three times with 0.5 ml of methanol. Following centrifugation, the supernatants were collected and combined with the original supernatant. The combined supernatants were evaporated to dryness under a stream of nitrogen. The cis-hydroxycotinine hemisuccinate was reconstituted in 0.6 ml of methanol. After spectrophotometry it was determined that 5.28 mg of product had been obtained. The material was then evaporated to dryness again.

The cis-hydroxycotinine hemisuccinate was dissolved in 280 µl of dimethylformamide. Eight mg of N-hydroxysuccinimide and 12 mg of dicyclohexylcarbodiimide were added, and the mixture stirred until all solids had dissolved. The mixture was incubated for 1 hour at room temperature with stirring.

A tube was prepared containing 1 ml of 0.1M carbonate buffer pH 9.0 and 2.8 mg glucose-6-phosphate dehydrogenase. To this tube were added seven 10 µl aliquots of the cis-hydroxycotinine hemisuccinate over a period of 1 hour, and mixing continued for 15 minutes after the last addition. The mixture was transferred to a dialysis bag and dialyzed overnight in the cold against 0.05M Tris-HCl pH 7.8. Dialysis was continued for an additional 26 hours with several changes of buffer. This conjugate was designated as RL-34.

10.1.4. Preparation of Glucose-6-Phosphate Dehydrogenase-Carboxycotinine Ligand Carboxycotinine was conjugated to glucose-6-phosphate dehydrogenase according to the following procedure:

To 1 ml of 0.1M sodium carbonate buffer, pH 9.0, were added 0.43 ml of glucose-6-phosphate dehydrogenase (2.8 mg), 20 mg of NADH (disodium salt), 10 mg of glucose-6-phosphate, and 300 µl of carbinol. The solution ("enzyme solution") was stored at 4° C. to chill.

To an empty test tube were added 22 mg of carboxycotinine, 11.5 mg of N-hydroxysuccinimide, 20.6 mg of dicyclohexylcarbodiimide, and 1.0 ml of dimethylformamide. This mixture was left at room temperature for 1 hour to allow the activated cotinine ester to form. After 1 hour, 10 µl of the reaction mixture were added to the cold enzyme solution at 15 minute intervals until a total of 70 µl were added (90 minutes total). Fifteen minutes after the final addition of reaction mixture, the modified enzyme was dialyzed against five changes of 1 liter each of 0.055M Tris-HCl buffer, pH 7.9, for at least three hours each.

10.1.5. Assay in Microtiter Plates

Strip microtiter plates were coated by addition of 100 µl of each of the conjugates at a protein concentration of 1 µg/ml to each well. The strips were covered with parafilm and incubated overnight at room temperature. The well contents were discarded, and wells washed twice with wash buffer. The wells were then incubated with 100 µl of antibody-peroxidase conjugate for 1 hour at r.t. Unbound conjugate was discarded and the wells washed twice with wash buffer. To each well were added 100 µl of wash buffer and 10 µl of cotinine standards, and the plates were mixed for 2 minutes. After mixing, 100 µl of liquid from each well was transferred to wells in uncoated plates, and 100 µl of tetramethylbenzidine (TMB) reagent were added. The plates were incubated for 7 minutes at room temperature, after which the reaction was stopped by addition of 50 μl of 2N sulfuric acid to each well. Absorbance was measured at 450 nm.

Residual peroxidase-antibody conjugate remaining bound to wells after release was measured by adding 200 μl of TMB to each well. After a 7 minute incubation, the reaction was stopped by addition of 50 μl of 2N sulfuric acid, and absorbance at 450 nm was measured.

A previously made conjugate of carboxycotinine-glucose-6-phosphate dehydrogenase was also assayed by this method.

10.2. Results

The results of assays with various hydroxycotinine-glucose-6-phosphate dehydrogenase conjugates are shown in Tables 5, 6 and 7.

TABLE 5

RELEASED ANTIBODY-PEROXIDASE CONJUGATE ($A_{450}$).

| COTININE STANDARD | CONJUGATE # | | | | | CARBOXY COTININE CONJU- |
|---|---|---|---|---|---|---|
| (μg/ml) | 24 | 25 | 26 | 29 | 30 | GATE |
| 0 | 0.971 | 1.049 | 1.030 | 0.442 | 0.662 | 0.498 |
| 0.5 | 1.911 | 2.071 | 1.990 | 0.753 | 1.051 | 0.505 |
| 2.0 | 2.529 | 2.739 | 2.635 | 0.948 | 1.436 | 0.526 |
| 10 | 2.804 | >3 | >3 | 1.355 | 1.974 | 0.728 |

TABLE 6

ANTIBODY-PEROXIDASE CONJUGATE ($A_{450}$) REMAINING ON WELLS.

| COTININE STANDARD | CONJUGATE # | | | | | CARBOXY COTININE |
|---|---|---|---|---|---|---|
| (μg/ml) | 24 | 25 | 26 | 29 | 30 | CONJUGATE |
| 0 | 2.474 | 2.514 | 2.513 | 1.893 | 2.097 | 2.707 |
| 0.5 | 2.403 | 2.368 | 2.440 | 1.776 | 1.937 | 2.746 |
| 2.0 | 2.213 | 2.347 | 2.360 | 1.739 | 1.879 | 2.730 |
| 10 | 2.051 | 2.253 | 2.298 | 1.695 | 1.790 | 2.786 |

TABLE 7

RELEASE ASSAY WITH CIS-HYDROXYCOTININE.

| COTININE | Absorbance at 450 nm | |
|---|---|---|
| CONC. (μg/ml) | RELEASED CONJUGATE | REMAINING CONJUGATE |
| 0 | 0.475 | 2.055 |
| 0.5 | 1.591 | 1.921 |
| 2.0 | 2.268 | 1.730 |
| 8.0 | 2.683 | 1.210 |

Release of enzyme-antibody conjugate activity is also shown graphically in FIG. 7. These results clearly indicate that use of modified analog as ligand provides the necessary difference in affinity for a release-type assay.

The cis-hydroxycotinine-glucose-6-phosphate dehydrogenase ligand was also tested in a homogeneous release assay such as described in Section 8.1.2., supra. After a 10 minute incubation of 10 μl of antibody binding reagent with a 10 μl of ligand in 140 μl of Tris buffer, 10 μl of sample were added. NAD and glucose-6-phosphate substrate (20 μl) were added after an additional 5 minute period, and $A_{340}$ read at 0, 2, 4, 8, 12, 16 and 20 minutes. Samples containing cotinine showed a more rapid increase in absorbance than sample with no cotinine. The results are shown in Table 8.

TABLE 8

HOMOGENEOUS RELEASE WITH CIS-HYDROXYCOTININE.

| Cotinine conc. (μg/ml) | OD Rate Change (mA/min) |
|---|---|
| 0 | 8.8 |
| 0.5 | 17.5 |
| 4.0 | 20.0 |

These results indicate that a microtiter plate format is ideal for screening for suitable low affinity ligands and ligand-enzyme conjugates. A ligand found to be suitable in a microtiter plate release assay can be used in a homogeneous release assay as well.

11. EXAMPLE: RELEASE IMMUNOASSAY FOR COTININE

In this Example 11, cotinine release assays using N-propylcarboxynorcotinine and N-isopropylcarboxynorcotinine as very low affinity relands is described. Cis 3'-hydroxycotinine was also used as a reland. The release assays were performed in both homogeneous (which can be compared to, but which is demonstrated to be superior than, the EMIT™ System (Rubenstein et al., 1972, Biochem. Biopys. Res. Comm. 47: 846)) and heterogeneous (microtiter plate, ELISA format) formats and compared to a conventional associative assay for cotinine. The results demonstrated that the release assays of the invention, based on dissociation, are more precise and exhibit less interference from cross-reactivity than known assays based on association. Moreover, the release assay of the invention has a standard curve that is linear, r 0.999, over a >10,000 fold range.

The following materials and methods sections set forth general descriptions of the reagents prepared and used in the assays, as well as the methods employed. The specific ligands used in each assay are identified in the results sections, and unless otherwise specified is N-isopropylcarboxynorcotinine.

11.1. Materials and Methods

Instrumentation included an SLT Lab instruments 340ATTC Microtiter Plate Reader, COBAS MIRA, and Varion VXR-200. Urine samples were from a general population previously analyzed for cotinine. Samples were stored at −20 degrees.

All chemicals were from Sigma Aldrich unless otherwise stated. Cis and trans-hydroxycotinine were purchased from the laboratory of George Neurath (See Neurath et al., supra)- Glucose-6-phosphate dehydrogenase was from Beckman. The Nicotine Metabolite Assay Kit, NiMA AutoMates™, and the ELISA Kits, Tobacco Screen®, and the Cotinine Trace Quantities, CotiTraq®, TMB chromogen system, anti-Cotinine antisera, peroxidase labelled anti-Cotinine, and Cotinine urine standards are commercially available from Serex, Inc. (Maywood, N.J.). Preparation of anti-cotinine antisera is described in Section 6.1.4., Supra.

11.1.1. Preparation of Relands

1-Isopropyl-4-carboxy-5-(3-pyridyl)-2-pyrrolidinone, (hereafter, N-isopropyl-4-carboxynorcotinine) and 1-propyl-4-carboxy-5-(3-pyridyl)-2-pyrrolidinone (hereafter, N-propyl-4-carboxynorcotinine) (FIG. 8) were prepared according to the method of Cushman & Castagnoli (1972, *J.Org. Chem.* 37:1268). Briefly, to a solution of 17 g of pyridine3-carboxy-aldehyde in 50 ml of benzene was added a benzene solution of 8 g isopropyl amine (or 8 g propyl amine) and 12 g molecular sieve pellets. The mixture was stirred at 20° C. overnight in a flask. The solution was filtered through two layers of Whatman No. 2 filter paper and evaporated under reduced pressure to give the imine as a yellow oil. The structure of the products was confirmed by $^1$H NMR.

N-isopropylcarboxynorcotinine and N-propylnorcotinine were prepared as follows. Twelve g of N-3-pyridylidene isopropyl imine or N-3 pyridylidene propyl imine and 15 g succinic anhydride were refluxed for 24 hours in 100 ml xylene. After the mixture cooled, the top layer was decanted and discarded. The residue brown oil was dissolved in 300 ml of 5% sodium bicarbonate solution, washed with two 250 ml portions of chloroform, and decolorized by absorption with 1 g activated charcoal. The suspension was filtered and the yellow filtrate heated on a steam bath to remove traces of chloroform. The pH was adjusted to 4.7 with phosphoric acid to precipitate the product. The crude carboxylic acid was collected by filtration and recrystallized from a boiling ethanol to give 4 g white crystal. The structures of the compounds were confirmed by $^1$H NMR.

11.1.2. Preparation of Glucose-6-Phosphate Dehydrogenase Conjugates

Conjugates of N-isopropyl-4-carboxynorcotinine, N-propyl-4-carboxy-norcotinine and cis 3'-hydroxycotinine to glucose-6-phosphate dehydrogenase were prepared according to the methods described by Rubenstein and Ullman (1975, U.S. Pat. No. 3,875,011). Briefly, to 1 ml of 0.1M sodium carbonate buffer, pH 9.0, were added 0.43 ml of glucose-6-phosphate dehydrogenase (2.8 mg), 20 mg of NADH (disodium salt), 10 mg of glucose-6-phosphate, and 300 μl of carbinol. The solution ("enzyme solution") was stored at 4° C. to chill.

To an empty test tube were added 26 mg of N-propyl or N-isopropylcarboxynorcotinine, 11.5 mg of N-hydroxysuccinimide, 20.6 mg of dicyclohexylcarbodiimide, and 1.0 ml of dimethylformamide. This mixture was left at room temperature for 1 hour to allow the activated cotinine ester to form. After 1 hour, 10 μl of the reaction mixture were added to the cold enzyme solution at 15 minute intervals until a total of 70 μl were added (90 minutes total). Fifteen minutes after the final addition of reaction mixture, the modified enzyme was dialyzed against five changes of 1 liter each of 0.055M Tris-HCl buffer, pH 7.9, for at least three hours each.

11.1.3. Reagents for the Homogeneous Release Assay

Reagent solutions for the homogeneous assay of cotinine were prepared as three separate solutions, reagents A, A+, and B. Reagent A consisted of glucose-6-phosphate dehydrogenase conjugate at a protein concentration of 0.74 μg/ml, 0.05M Tris buffer, 5 mM $MgCl_2$, 0.5 mM EDTA, 1.75 mg/ml glucose-6-phosphate, 0.5% BSA, and preservatives at pH 7.9. Reagent A+ consisted of antisera in reagent A buffer. Reagents A and A+ were mixed prior to use to form working solution A, which is stable for one week at 4° C.

Reagent B consisted of NAD at 3.3 mg/ml in 0.02M Tris buffer, pH 7.0.

Cross-reactivity was tested with cotinine and/or trans-3'-hydroxycotinine solutions prepared as follows. To 10 ml of a negative urine pool were added 100 μg of cotinine or trans-3'-hydroxycotinine. The mixture was vortexed and serially diluted into the same negative urine standard to make solutions of 5, 2.5, 1.25, 0.62, 0.31 and 0.16 μg/ml of cotinine or trans-3'-hydroxycotinine.

To prepare the 1:3, cotinine:trans-3'-hydroxycotinine, solution, a 10 ml aliquot of negative urine standard was spiked with 100 μg of continine and 300 μg of trans-3'-hydroxycotinine. This solution was vortexed and serially diluted into the same negative urine standard to form dilutions of 5 (15), 2.5 (7.5), 1.25 (3.75) 0.62 (1.87). 0.31 (0.94), 0.16 (0.48) μg/ml of cotinine (hydroxycotinine).

Cross-reactivity was calculated using the following formula;

$$\frac{\text{concentration found (µg/ml)}}{\text{concentration of cross reactant (µg/ml) in sample}} \times 100\%$$

11.1.4. Assay Formats

ELISA format. Corning microtiter plates were coated overnight with 100 μl of either glucose-6-phosphate dehydrogenase conjugated to cis-hydroxycotine, N-propyl-norcotinine or N-isopropyl-norcotinine at 1 μg protein per ml of PBS; the wells were emptied, dried and stored with dessicant until use. To activate for release, the plate was incubated <1 hour with 100 μl of peroxidase labelled affinity purified anti-cotinine antibody. Excess antibody was removed by 2 washes with PBS in 0.05% Tween 20.

To a microtiter plate coated with a release ligand-antibody (reland) complex, 10 μl of urine/standard and 90 μl of distilled water were added to each well. After 2 minutes, 50 μl of the supernatant were transferred to uncoated wells containing 100 μl of TMB and incubated for 10 minutes. The reaction was stopped with 100 ml of 1N $H_2SO_4$ and $A_{450}$ was read.

Homogeneous Release Assay. The homogeneous assay of the present invention, was performed in the AutoMates™ format, utilizing the same enzyme system and the same reagents as the conventional homogeneous associative assay, but modified as follows to become a dissociative reaction.

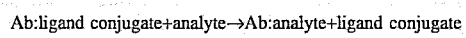

Before use, reagent A (enzyme conjugate in buffer) and reagent A+ (antisera in buffer) were mixed for a minimum of one hour. The reaction was started by addition of sample and NAD. As in the associative assay, enzyme activity was measured by monitoring the formation of NADH at $A_{340}$ nm, and enzyme activity is directly related to the concentration of analyte in the sample.

The homogenous assay of the invention using AutoMates™ was performed on the COBAS MIRA according to the application sheet parameters. Two hundred μl of reagent A were incubated with 10 μl of reagent B (NAD) and the mixture was incubated for 25 seconds. The absorbance was read over the final 200 seconds. Total time of the assay was 5.0 minutes. Greater sensitivity of a sample containing 10 ng/ml of analyte was observed with a 25 μl sample.

Associative Homogeneous Assay. The NiMA AutoMates™ format is a homogeneous, associative, competitive assay, like that described by Rubenstein, Schneider, and Ullman (1972, supra). There are two steps to the immune reaction:

jugate +Ab:analyte

Briefly, sample was pre-incubated with antisera for several minutes. Into this reaction mixture was added glucose-6-phosphate dehydrogenase conjugated with cotinine. Antibody that has not interacted with cotinine in the sample binds to cotinine on the glucose-6-phosphate dehydrogenase. The binding of antibody to the enzyme-linked ligand inhibits enzyme activity, thus the enzyme activity is directly related to the concentration of analyte in sample. Enzyme activity of glucose-6-phosphate dehydrogenase was measured by monitoring at $A_{340}$ nm the formation of NADH, which forms as the enzyme oxidizes glucose-6-phosphate to glucono-ε-lactone-6-phosphate and reduces NAD to NADH.

NiMA AutoMates™ was performed on the COBAS MIRA according to the application sheet parameters. Two hundred µl of reagent A were incubated with 10 µl of sample at 37 degrees for 75 seconds. Fifty µl of reagent B were added and the mixture was incubated for 25 seconds. The absorbance was read over the final 250 seconds. Total time of the assay was 5.83 minutes.

11.2. Results

11.2.1. Heterogeneous Release Assay (Elisa Format)

Release of labelled antibody complexed to solid phase was detected in supernatant when free cotinine was present in sample (FIG. 9). Unlike conventional competitive immunoassays, absorbance or signal was directly proportional to analyte concentration.

The cis-hydroxycotinine conjugate bound and released the antibody most efficiently, but had the highest background.

11.2.2. Homogeneous Format

Dose response curves for the associative (NiMA) and release homogeneous assays demonstrate the greatly increased range of the release assay (FIG. 10). Comparison of the associative and release formats is presented in Table 9.

TABLE 9

COMPARISON OF A HOMOGENEOUS DISSOCIATIVE ASSAY FOR COTININE AND A HOMOGENEOUS ASSOCIATIVE ASSAY FOR COTININE (NiMA).

|  | RELEASE | NiMA |
| --- | --- | --- |
| Final Antisera Dilution | $4.8 \times 10^{-3}$ | $2.4 \times 10^{-3}$ |
| Final Conjugate Concentration | 0.51 µg/mL | 0.03 µg/mL |
| Antisera Dilution/µg Conjugate | $9.6 \times 10^{-3}$ | $80 \times 10^{-3}$ |
| Lower Limit | 0.01 µg/mL | 0.05 µg/mL |
| Upper Limit | 1000 µg/mL | 2 µg/mL |
| Time | 5 min | 5.8 min |

Table 9 shows that the release assay utilizes 17-fold more enzyme and two-fold more antibody than the associative assay. But the increased enzyme and antibody do not result in decreased sensitivity as they do in associative immunoassays: smaller amounts of all reactants can be utilized in release, but this limits upper range of the assay. FIG. 11 shows the range of the assay, 0.01–100 µg/ml. In the example shown, a seventeen-fold increase in reactants yields a greater than 1,000-fold increase in range of the assay, with no loss of sensitivity at the low end of the curve. This formulation is sensitive to 10 ng/ml and can be used for quantitating saliva samples. The antibody to enzyme ratio of the release to associative assays is 10:80; that is the associative assay uses 8-fold more antibody per enzyme molecule than the release. In the release assay all antibody molecules can be bound to ligand conjugated to enzymes and are capable of being released by analyte. In the associative assay there is a large excess of antibody, which decreases reaction time. The ability of the release assay to monitor the activity of a much larger percentage of the antibody in the reaction mixture increases sensitivity and decreases background noise and reaction time.

11.2.3. Cross-Reactivity: Trans-hydroxycotinine

The specificity of the release assay relative to the associative assay was confirmed by comparing the release and association formats for cross-reactivity with trans-3'-hydroxycotinine (Table 10).

TABLE 10

INTERFERENCE OF TRANS-HYDROXYCOTININE IN RELEASE AND ASSOCIATIVE (NiMA) HOMOGENEOUS ASSAYS FOR COTININE.

| SPIKE CONC. (µg/mL) | COTININE SPIKE | | TRANS-HYDROXY-COTININE SPIKE | |
| --- | --- | --- | --- | --- |
|  | CONCENTRATION FOUND (µg/mL) | % RECOVERY | CONCENTRATION FOUND (µg/mL) | % RECOVERY |
| RELEASE ASSAY | | | | |
| 10 | 9.03 | 90 | 1.69 | 16.9 |
| 5 | 4.22 | 84 | 0.72 | 14.4 |
| 2.5 | 2.15 | 86 | 0.29 | 11.6 |
| 1.25 | 1.15 | 92 | 0 | 0 |
| 0.62 | 0.63 | 102 | 0 | 0 |
| 0.31 | 0.25 | 81 | 0 | 0 |
| 0.16 | 0.14 | 88 | 0 | 0 |
| AVERAGE |  | 89 |  | 6.1 |
| NiMA | | | | |
| 10 | 11.85 | 119 | 1.87 | 18.7 |
| 5 | 5.6 | 112 | 0.85 | 17 |
| 2.5 | 2.03 | 81 | 0.44 | 17.6 |
| 1.25 | 1.59 | 127 | 0.21 | 16.8 |
| 0.62 | 0.59 | 95 | 0.17 | 27.4 |
| 0.31 | 0.49 | 158 | 0.11 | 35.5 |
| 0.16 | 0.13 | 81 | 0.08 | 37.5 |
| AVERAGE |  | 110 |  | 24.4 |

The release assay showed one-fourth the cross-reactivity with hydroxycotinine of the associative assay. In the release assay there was no cross-reactivity at the low end of the curve. The greatest amount of interference in the associative assay was seen at the low end of the curve. To evaluate the actual effect of trans-3'-hydroxy cotinine on the assay of urine samples, samples were spiked with cotinine:trans-3'-hydroxycotinine in a 1:3 ratio (this is the ratio reported to exist in smokers' urine (Engvall et al., 1971, Immunochemistry 8:871)) and assayed in both release and associative. homogeneous assays (Table 11).

TABLE 11

CROSS REACTIVITY OF TRANS-HYDROXCOTININE IN THE PRESENCE OF COTININE IN THE RELEASE AND THE ASSOCIATIVE (NiMA) HOMOGENEOUS ASSAYS FOR COTININE.

| COTININE (TRANS HYDROXY-COTININE) μg/mL | RELEASE | | NiMA | |
|---|---|---|---|---|
| | COTININE CONC. FOUND (μg/mL) | % COTININE RECOVERY | COTININE CONC. FOUND (μg/mL) | % COTININE RECOVERY |
| 10 (30) | 16.82 | 168 | >20 | >200 |
| 5 (15) | 7.55 | 151 | 14.21 | 284 |
| 2.5 (7.5) | 3.69 | 148 | 4.38 | 175 |
| 1.25 (3.75) | 1.45 | 116 | 2.29 | 183 |
| 0.62 (1.9) | 0.92 | 155 | 1.82 | 294 |
| 0.31 (0.93) | 0.4 | 129 | 0.54 | 174 |
| 0.16 (0.48) | 0.23 | 144 | 0.37 | 231 |
| AVERAGE | | 144 | | 220 |

Trans-3'-hydroxycotinine contributed to cotinine quantitation in both the release and the associative assays. The contribution is rather constant across the range of the assay in both formats but results in an average 220% recovery in the associative assay but only 144% in the release assay, indicating that the release assay is less subject to interference by cross-reactivity, therefore reducing the potential for false positive results in an assay for cotinine.

The results for cross-reactivity in Table 10 suggest that trans-hydroxycotinine present in a sample at the expected 3:1 ratio to cotinine would increase the apparent detection of cotinine by about 45% (3 times about 15% cotinine recovery). Thus the expected recovery of cotinine in the release assay reported in Table 11 is about 145%. In fact, the average percent cotinine recovery was about 144%. A similar analysis for the associative (NiMA) format indicates that the same 3:1 trans-hydroxycotinine to cotinine ratio would increase the apparent cotinine recovery by about 60% (3×20%). Thus the expected recovery of cotinine in the associative (NiMA) assay reported in Table 11 is 160%. However, the average % cotinine recovery is 220%, and ranged as high as 294%. Thus there appears to be a "synergistic" effect of trans-hydroxycotinine on cotinine detection, so that the presence of transhydroxycotinine skews results in the associative assay for cotinine in an unexpected, and therefore perhaps uncorrectable, way.

The release assay exhibits cross-reactivity as predicted, but the associative format shows average recoveries of 220%, almost double that predicted by the simple cross-reactivity data. This demonstrates that the associative assay is more subject to interference than release.

11.2.4. Cross-Reactivity of N-Isopropyl-4-Carboxy Norcotinine

To further test the stability and releasability of the antibody-ligand complex we characterized the ability of N-isopropyl-4-carboxynorcotinine to interfere in the various release assays, all of which used the same antibody. Results are shown in Table 12.

TABLE 12

CROSS REACTIVITY FOR N-ISOPROPYL-4-CARBOXY-NORCOTININE IN ASSOCIATIVE AND RELEASE ASSAYS.

| SPIKES URINE (μg/mL) | % CROSS REACTIVITY | | |
|---|---|---|---|
| | CotiTraq ® | Release | NiMA |
| 0.24 | | 0% | <0 |
| 0.5 | 0% | 0% | <0 |
| 2 | 0% | 0% | <0 |
| 4 | 0% | 0% | 0.05% |
| 10 | 0.3% | 0% | 0.11% |
| 100 | 0.3% | 0.4% | 0.24% |

The ligand N-isopropyl-4-carboxy cotinine showed less than 0.4% cross-reactivity, even in concentrations as high as 100 μg/ml. The ligand shows no cross-reactivity with the antibody complexed to it on G-6-P-DH until 100 μg/ml, at which point cross-reactivity of 0.4% was detected. N-isopropyl-4-carboxy-cotinine interfered more in the conventional NiMA and CotiTraq® Assay format than in the release assay, indicating that it is not a competitor for the antibody in the release format.

The release homogeneous assay and conventional homogeneous and conventional ELISA formats were also compared. The release heterogeneous assay, NiMA AutoMates™ and Tobacco Screen® (ELISA) assays for cotinine were compared using a cotinine equivalent cutoff of 0.5 μg/ml (0.5μg/ml is considered equivalent to urine composition of 0.25 μg/ml cotinine, 0.75 μg/ml hydroxycotinine in Tobacco Screen® and NiMA, and 0.35 μg/ml cotinine in the release assay of cotinine). Table 13 shows that release correlates 100% with Tobacco Screen®. Tobacco Screen® correlates 100% with HPLC results using an HPLC cutoff of 200 ng/ml and a Tobacco Screen® cutoff of 400 ng/ml.

TABLE 13

COMPARISON OF RELEASE HOMOGENEOUS COTININE ASSAYS WITH THE ASSOCIATIVE ASSAYS, TOBACCO SCREEN ® (ELISA) AND NiMA (HOMOGENEOUS), USING 0.5 μg/mL CUTOFF FOR ALL ASSAYS.

| TOBACCO SCREEN ® | | | NiMA | | |
|---|---|---|---|---|---|
| Release | + | − | Release | + | − |
| + | 106 | 0 | + | 106 | 0 |
| − | 0 | 34 | − | 0 | 34 |
| n = 140 | | | n = 140 | | |

11.2.5. Assay Precision

The release and NiMA homogeneous assays for cotinine were evaluated for precision on a COBAS MIRA using negative, 0.5 μg/ml and 2 μg/ml urine samples (Table 14). Precision is used to indicate the coefficient of variation of repetitive tests on the same sample. The release assay showed more than a two-fold improvement in precision over the associative assay. Even though reactant concentrations are 17-fold higher than NiMA, the release assay had better precision.

TABLE 14

PRECISION OF THE RELEASE AND THE
ASSOCIATIVE NiMA HOMOGENEOUS ASSAYS FOR
COTININE. RESULTS STATED ARE REACTION RATE
IN mA/MIN.

| Negative Control<br>0.0 µg/mL | Cutoff Control<br>0.5 µg/mL | Positive Control<br>2.0 µg/mL |
| --- | --- | --- |
| RELEASE | | |
| n = 15 | n = 15 | n = 15 |
| avg = 177.79 | avg = 185.4 | avg = 194.56 |
| SD = 0.88 | SD = 0.89 | SD = 0.81 |
| CV = 0.5% | CV = 0.5% | CV = 0.4% |
| NiMA | | |
| n = 15 | n = 15 | n = 15 |
| avg = 49.52 | avg = 55.86 | avg = 58.27 |
| SD = 0.69 | SD = 0.75 | SD = 0.78 |
| CV = 1.3% | CV = 1.3% | CV = 1.3% |

11.3. Discussion

11.3.1. Heterogeneous Format

A release ELISA assay well contains less than ⅕ the antibody utilized in conventional ELISA assays. Sensitivity is enhanced as a result because non-specific activity decreases. Sensitivity is also enhanced by the almost ten-fold higher enzyme activity of the released peroxidase-labelled antibody.

In the ELISA format this end point release assay reduces the time for the assay from 1.5 hour to under 15 minutes (2 minutes for the release reaction and 10 minutes for TMB color development). Time could be further shortened, for example, by automating the assay steps such as by running a rate reaction assay on an automated instrument. The release assay also reduces the number of assay steps by at least half. A further advantage is the release gives a positive signal in the presence of analyte.

11.3.2. Homogeneous Format

In the homogeneous assay format, sensitivity is further enhanced by the fact that released peroxidase-labelled antibody has much higher activity than enzyme on the plate. That is, if one measures released peroxidase conjugated antibody and that remaining on the plate, one can see that a 0.1 O.D. drop in plate absorbance can result in generation of 2.0 O.D. units in the supernatant. This 10- to 20-fold enhancement of free enzyme activity is probably in large part due to a decrease in the effects of diffusion on the released enzyme reaction rate.

The range of the release assay is extended because the release assay is a system that starts in equilibrium. It is therefore possible to use higher starting concentrations of enzyme complex without increasing noise or losing low-end sensitivity. In conventional immunoassays, addition of more reagents changes the sensitivity of the assay by shifting final equilibrium conditions. Enzyme concentration demonstrating release assay were 0.50 µg/ml as compared to 0.03 µg/ml for conventional homogeneous (associative) assays. However, the conventional type assay had about 8 times as much antibody:enzyme as the release assay. The use of monoclonals will further improve the ratio of antibody to enzyme in the release format. The ratio of antibody to enzyme determines assay sensitivity.

While other assay systems that involve dissociation of preformed antibody-ligand complexes (Cocola et al., 1979, *Analytical Biochem.* 99:121–8-Hinds et al., 1984, *Chin.Chem.* 30:1174–8; Hinds et al., 1985, *Chin.Chem.Acta* 149:105–15) have utilized competitive ligands as binding partners, the release assay is a non-competitive system. This is demonstrated in Table 12, supra, where release ligand (or reland) cannot compete the antibody off the antibody-ligand complex. It is also noteworthy that unlike the release assay of the present invention, the competitive dissociation assays described by Cocola et al., Hinds et al., 1984 and Hinds et al., 1985, supra, have not shown significant improvement over associative methods of immunoassay. Although the, present invention is not bound by any particular theory, we hypothesize that antibody binds to the release ligand via very low affinity interaction, and in the absence of higher affinity binding partners, antibody undergoes a conformational change to a metastable complex that is releasable and has a time stable affinity constant for release. The complex may become too stable, as observed with conventional ligand conjugates. N-isopropyl-norcotinine was designed to provide a bulky group at a nonimmunologically critical site to allow dissociation after equilibrium.

The rapid dissociation of the reland complex in the presence of ligand may be analogous to turnover in antibody Catalysis (Benkovic et al., 1990, *Science* 250:1135–8) in which antibody prepared to a transition state substrate conformation binds a substrate, induces the transition state conformation in the substrate, and then releases the cleaved substrate rapidly since the products no longer appear in the transition state.

11.3.3. Cross-Reactivity

The release assay is less subject to cross-reactivity. More importantly, it was not subject to the synergistic type of cross-reactivity that was observed with conventional immunoassay. We have observed this synergistic enhancement of interference in other conventional immunoassay formats. This may be a generalized phenomenon and perhaps all cross-reactivity ought to be reported as % cross-reactivity seen in the presence of analyte at 50% binding, so that the true contribution to the assay can be assessed.

11.3.4. Assay Precision

The two-fold improvement in precision seen with the release assay of the invention is probably multifactorial: the starting system is in equilibrium and only one reaction—dissociation—occurs, and the matrix, as evidenced by lowered cross-reactivity, probably has less effect on the reaction.

11.4. Conclusion

We have developed an assay method utilizing the ability of antibodies to assume an induced fit with a binding partner for which it has very low affinity, the release ligand, or reland. The release assay provides a preformed receptor-reland complex, which can be rapidly dissociated in the presence of analyte. The release system can be used in all immunoassay formats. The release assay has inherent advantages over conventional or associative assays:

1. By eliminating one step in the immune reaction, release saves time and steps and possible sources of error, thereby shortening assay time and simplifying assay techniques.
2. Release, i.e., dissociation, is inherently less subject to interference making it more accurate.
3. The ability to monitor all antibody in the assay reduces noise and makes a 1000–10,000-fold sensitivity range possible. This methodology, using more sensitive markers, extends the theoretical range both up and down from that available in conventional assay formats. Addition of more reactants does not lower sensitivity as in conventional immunoassays, but extends the upper range of sensitivity. An important advantage of release is the mild conditions under which the dissociation occurs. This allows the solid phase or complex to be regenerated. This should advance the possibilities for biosensors. A major problem with biosensors is that the solid phase is usually a disposable; with the release assay the solid phase can be continually regenerated.

5. The large range, the positive correlation with presence of analyte, and the low noise of the system indicates that the release assay format can be used to screen for many analytes in one reaction mixture.

12. EXAMPLE: RELEASE ASSAY FOR A COCAINE METABOLITE

Benzoylecgonine is a metabolite of cocaine. Release immunoassays that allow detection of soluble benzoylecgonine in a sample are described below. In particular, release of an enzyme-labeled antibenzoylecgonine antibody can be detected in assay solution supernatant when free benzoylecgonine is present. The following example demonstrates an effective release assay for benzoylecgonine. Two assay parameters, the effect of the relative amount of antibody-label conjugate incubated on a ligand-protein coated plate and incubation time after addition of sample on detection of released label, were investigated.

12.1. Materials and Methods

Using standard techniques, ecgonine was conjugated to BGG via a bulky linker (p-aminobenzoic acid). Anti-benzoylecgonine-peroxidase conjugate was prepared using standard techniques.

12.1.1. Titration of Conjugate

Microtitre plates were coated with benzoylecgonine-BGG ligand. After washing, 100 µl of antibody-peroxidase conjugate were added to each well at either 1:500 or 1:1000 dilution and incubated at to for 60 min and washed twice with wash buffer. Benzoylecgonine (BE) standard solutions (100 µl) were added to individual wells. Benzoylecgonine was present at the following concentrations in distilled water or urine: 0, 0.025, 0.3, and 5.0 µl/ml. After adding sample, plates were incubated 10 min with shaking at r.t., and 100 µl of supernatant were added to replicate wells of an uncoated microtitre plate. To each well of assay supernatant were added 100 µl of 2x TMB substrate solution. The plates were incubated 6 min at r.t., and the reaction stopped by addition of 50 µl of 2 N $H_2SO_4$ to each well. Absorbance at 450 nm was measured in a plate reader.

12.1.2. Assay for Influence of Incubation Time and Matrix Composition

The procedure described above (Section 12.1.1.) was followed. To detect the effect of matrix composition, standards in a synthetic urine matrix were diluted in deionized water. To assay the effect of incubation time, i.e., time needed to detect release of labeled antibody, peroxidase labeled antibenzoylecgonine ecgonine-BGG-coated plates were incubated 0, 2 and 10 minutes after addition of free benzoylecgonine before transfer of supernatant to a clean microtiter plate.

12.2. Results

Free benzoylecgonine in sample resulted in release of antibody-peroxidase conjugate. The amount of conjugate released correlated with the amount of conjugate added to the benzoylecgonine-BGG coated plate as well as with the amount of analyte present in the sample (Table 15). Thus more conjugate is released from incubation with a 1:500 than a 1:1000 diluted solution.

TABLE 15

RELEASE OF ANTI-BENZOYLECGONINE-PEROXIDASE FROM ECGONINE-PABA-BGG-COATED PLATE.

| Ecgonine conc. | $A_{450}$ of Released Anticotinine-Peroxidase | |
|---|---|---|
| (µg/ml) | 1:500 | 1:1000 |
| Stds in Water | | |
| 0 | 0.881 | 0.574 |
| 0.025 | 1.541 | 0.944 |
| 0.30 | 2.465 | 1.630 |
| 5.0 | 2.859 | 2.218 |
| Stds in Urine | | |
| 0 | 0.234 | 0.112 |
| 0.025 | 0.493 | 0.255 |
| 0.30 | 1.182 | 0.630 |
| 5.0 | 1.901 | 1.010 |

Matrix effects are also evident from the data in Table 15. In particular, release appears to be more effective in water than in urine. These results are expected since matrix is known to affect antibody antigen reactions. Nevertheless, the relative release of antibody-enzyme conjugate is not affected by matrix composition. This relationship can be seen by comparing the ratio of $A_{450}$ when free benzoylecgonine is present to $A_{450}$ blank in each matrix (FIG. 12). Thus, the matrix effect appears to result from inhibition of enzyme by components in urine and does not appear to affect the amount of antibody-enzyme conjugate released.

The time of incubation appears to have minimal effect on enzyme activity in supernatant as shown graphically (FIG. 13).

12.3. Discussion

These results indicate that release of labeled antibody from a ligand coated plate is proportional to the amount of labeled antibody added to the plate.

The results also indicate that while sample matrix affects the absolute enzyme label activity in release supernatant, this effect can be corrected for by normalization over baseline control activity. Generally, normalization of various samples allows comparison and quantification of free ligand, in this case free benzoylecgonine, present in the sample.

Finally, the results in FIG. 13 indicate that release is nearly complete almost immediately after addition of free ligand, demonstrating that release assays may be run in short period of time.

13. EXAMPLE: RELEASE ASSAY ON ANTIBODY-COATED MEMBRANES

In a particular embodiment, presence of soluble analyte may be detected by release of labeled ligand from an antibody-coated solid phase support, e.g., a membrane. This example demonstrates release of labeled ecgonine from a complex with solid phase antibody specific for benzoylecgonine.

13.1. Materials and Method

13.1.1. Labeled Ligand

Ecgonine was linked to alkaline phosphatase via a spacer linker. In 20 ml of DMSO (Sigma) were dissolved 40 mg ecgonine (Alltech), 32 mg N-hydroxysuccinimide (Sigma) and 56 mg of 1-ethyl-(3-aminopropyl)carbodiimide (Pierce) at r.t. for hrs. A solution of 25 mg N-(4-aminobenzyl)-6-aminocaproic acid (Aldrich) in 0.5 ml DMSO was added to 2.0 ml of 0.2M sodium bicarbonate, pH 7.8, and this mixture was added to the activated ecgonine solution. The resulting solution was mixed for 1 hr. at r.t. and held at 4° C. overnight. To 1.0 ml of activated ecgonine-linker solution were added 0.3 ml of 10 mg/ml N-hydroxysuccinimide and 16.7 mg/ml 1-ethyl-3-(3-dimethylamino)carbodiimide (Sigma) in DMSO, and the resulting mixture shaken for 4 hrs at r.t. To 1 ml of a solution of 1 mg/ml alkaline phosphatase (Biozyme ALPI IIG, 1650 U/mg) were added 0.65 ml of activated ecgonine-linker, and the mixture incubated 2 hrs at r.t., then held at 4° C. overnight. The product was dialyzed in the cold against 0.5M carbonate buffer, pH 7.8, for 8 hours, with dialysis fluid changed every 4 hours.

13.1.2. Antibody-Coated Latex Membrane Assays

A suspension of 0.5 ml of polystyrene latex particles, 0.776 microns (IDC) mixed with 3.5 ml of phosphate buffer pH 7.5 was prepared. Goat antirabbit IgG, Fc fraction, was diluted to 0.5 mg/ml in phosphate buffer (0.2 ml to 4 ml). The two were mixed by inversion and incubated at room temperature for 1 hour, and then stored at 4° C. 1 ml of this latex preparation was centrifuged for 5 minutes at 3000 RPM, washed with 0.01M phosphate buffer, pH 7.5, and recentrifuged. The latex particles were resuspended in 5 ml of phosphate buffer containing 0.1% Tween 20. 55 µl of rabbit antibody against benzoylecgonine were diluted in 5 ml of the Tween/phosphate and added to the latex suspension. The mixture was gently mixed at room temperature for 60 minutes. It was then centrifuged for 5 minutes at 3000 RPM, washed twice with Tween/phosphate with centrifugation and resuspension. The preparation was resuspended in Tween/phosphate buffer containing 0.1% sodium azide.

Membranes were prepared by soaking 0.45 µ filtration membranes in 80 µl of Tween/phosphate buffer, and 20 µl of anti-benzoylecgonine-coated latex were added and allowed to absorb. Then 10 µl of labeled ecgonine were added to each latex spot. The membranes were incubated 3 hrs at r.t. to allow stable receptor-ligand complex to form and subsequently washed three times with phosphate buffer containing 0.1% Tween 20. Sample or standard was added (100 µl), and the membrane incubated 10 min. at r.t. with shaking. The test was generally run as a visual test by adding substrate directly to membranes where it is washed away released ligand-enzyme samples. Decreased color-intensity was proportioned to the benzoylecgonine concentration in the sample.

For quantitating release the liquid phase (supernatant) was collected by filtration and 50 µl aliquots were added to wells of microtiter plates. To each well were added 100 µl of p-nitrophenylphosphate (Sigma) in diethanolamine buffer, pH 9.7, and the plates were incubated 30 min at room temperature. Absorbance at 405 nm was measured.

13.2. Results

The results of this assay are shown in Table 16.

TABLE 16

| Enzyme Activity of Liquid Phase | |
| --- | --- |
| BENZOYLECGONINE CONC. (µg/ml) | $A_{405}$ |
| 0 | 0.214 |
| 5 | 0.352 |

These results demonstrate release of ecgonine-linker-alkaline phosphatase from the latex-antibody preparation when free benzoylecgonine is present in sample.

14. EXAMPLE: RELEASE ASSAY FOR TETRAHYDROCANNABINOL (THC)

A solid phase membrane assay, similar to that described in Section 13, supra, has been prepared to allow detection of tetrahydrocannabinol, the major active component of marijuana.

14.1. Materials and Methods

14.1.1. Preparation of Membranes

Polyclonal antibodies (sheep) to THC were used. Ammonium sulfate purified antibody, 13 mg/ml in 0.5M carbonate buffer pH 9.3 in volume of 3 µl, were absorbed to 5 mm disks of Gelman KV3000 ultrabind membranes. The disks were allowed to dry for 30 minutes at room temperature, and then were treated with 0.1% (w/v) bovine serum albumin in carbonate buffer for 15 minutes at room temperature. Excess albumin was removed by aspiration, and membranes were washed for 10 minutes at room temperature with a buffer consisting of 2% (w/v) glucose and 0.01% (w/v) 2,6-di-tert butyl-4-methylphenol (BHT) (Aldrich) in 0.5M carbonate buffer, pH 9.3. Disks were allowed to dry at room temperature and stored at 4° C.

14.1.2. Preparation of Ligand

Two mg of 9-carboxy-11-nor-delta-9-tetrahydrocannabinol (C-THC) were dissolved in 0.2 ml of dimethylsulfoxide, and 0.74 mg of n-hydroxysuccinimide were added. After reaction at room temperature for 2 hours, 0.5 ml of this mixture were added to 5 mg of alkaline phosphatase in 3 ml of phosphate buffered saline (PBS). The entire reaction mixture was mixed overnight at room temperature.

14.1.3. Assay Procedure

Disks containing 3 µl of anti-THC antibody at 1:10 dilution were placed in wells of microtiter plates. To these disks were added 100 µl of the THC-alkaline phosphatase ligand at a 1:2000 dilution. Plates were incubated for 30 minutes at room temperature. To assess the effect of various components on the stabilization of dried receptor-ligand complex, various formulations were used to wash the complex prior to drying. Wells were washed with Tris buffer containing 0.1% Tween 20 or with Tris buffer containing glucose. The disks were then allowed to dry and 200 µl of standards containing 0 or 10 µg/ml THC were added to the disks in wells. The assay could then be read visually by adding substrate to the membrane and noting a definite fading of color when THC effected release. The reaction could also be quantitated as described further. The plates were incubated for 30 min at room temperature and 100 µl of supernatant from each well were transferred to wells in a clean replicate microtiter plate.

To each well of the replicate microtiter plate were added 100 μl of p-nitrophenylphosphate (Sigma). The plates were incubated for 15 minutes at room temperature, and absorbance read at 405 nm.

The remaining incubation mixture of solid phase antibody and conjugate was incubated for 30 min at 37° C. and 100 μl of this supernatant was transferred to replicate wells in clean microtiter plates. To each well were added 100 μl of p-nitrophenylphosphate and the plates were incubated for 15 min at room temperature, and absorbance measured at 405 nm.

14.2. Results

The results of this assay are shown in Table 17.

TABLE 17

RELEASE OF LABELED THC-ALKALINE PHOSPHATASE CONJUGATE AS A FUNCTION OF STABILIZATION OF RELEASE COMPLEX.

| SAMPLE | 30' INCUBATION ROOM TEMP | | 30' INCUBATION, ROOM TEMP. PLUS 30' AT 37° C. | |
|---|---|---|---|---|
| | TRIS/ TWEEN WASH | TRIS/ TWEEN/ GLUCOSE WASH | TRIS/ TWEEN WASH | TRIS/ TWEEN GLUCOSE WASH |
| 0 μg/ml THC | 0.101 | 0.111 | 0.129 | 0.212 |
| 10 μg/ml THC | 0.134 | 0.152 | 0.260 | 0.484 |

These results show the optimization of incubation times and formulation of washing buffer on the release of THC:alkaline phosphatase conjugate from antibody bound to membranes. In particular, the presence of glucose in the washing buffer enhances released enzyme activity in the supernatant. Most importantly, these results indicate preference of the antibody for the analyte in the sample, thus demonstrating an effective release assay for THC.

It should be noted that the release reaction visualized on membranes was much more dramatic.

15. EXAMPLE: RELEASE ASSAY FOR BETA-BLOCKERS

A homogeneous release assay for betablockers is presented. Detection of beta-blockers is useful for monitoring patients on these drugs. In particular, the stability of antibody complexes with ligand was tested.

15.1. Materials and Methods

15.1.1. Ligand: Analyte-Enzyme Conjugate

Atenolol acid (6.5 mg) (Imperial Chemical Industries) was dissolved in 0.125 ml of 0.1M sodium carbonate with the aid of 0.015 ml of 1 N HCl. After dissolution, 0.1 ml of deionized water and 0.25 ml of dimethylsulfoxide were added, followed by 6 mg of N-hydroxysuccinimide and 10 mg of EDC. The reaction mixture was kept at room temperature for 2 hours. To a glass tube were added 1 ml of 0.1 sodium carbonate buffer, pH 9.0, and 2.8 mg of glucose-6-phosphate dehydrogenase; after dissolving, 20 mg of reduced nicotine adenine dinucleotide (NADH), 10 mg of glucose-6-phosphate and 0.3 ml of carbitol [2-ethoxy-ethoxy) ethanol] were added. This mixture was kept at 4° C. for 1 hour.

One hundred forty μL of the activated atenolol were added to the glucose-6-phosphate dehydrogenase reaction vessel over a period of 90 minutes, in aliquots of 10 μl. Fifteen minutes after the last addition the material was transferred to a dialysis bag and dialyzed overnight in the cold against 2 l of 0.05M Tris-HCl, pH 7.9. The next day dialysis was continued for 8 hours with three changes of fluid.

15.1.2. Assay System

Reagent A (160 μl) was prepared with 1 μl of antiserum (rabbit) against 4-hydroxypropranolol, and 12 μl of 0.11M glucose-6-phosphate in 0.05M Tris buffer, pH 7.9, 3.3 mM magnesium chloride.

Reagent B (30 μl) was prepared with 10 μl of conjugate of 1:500 dilution, and 8 μl of 0.1M nicotine adenine dinucleotide in 0.05M Tris buffer, pH 7.9.

A and B were mixed for 10 seconds and 10 of sample or standard were added, followed by mixing for 10 seconds. The mixture was incubated for the indicated times at 37° C. and absorbance at 340 nm measured.

15.2. Results

15.2.1. Stability of Antibody-Conjugate Complex

These experiments were designed to determine the stability of the antibody/beta-blocker-enzyme complex.

The complex was made up with 1.41 ml of 0.05M Tris-HCl, pH 7.8, 10 μl of undiluted antibody, 80 μl of 0.1M NAD and, and 100 μl of conjugate at 2 mg/ml and kept at room temperature for the indicated time periods. At specified times, samples containing free 4-hydroxpropanolol were added to aliquots of the complex and the mixture was incubated for 5 min at room temperature. The reagent containing glucose-6-phosphate was then added, and absorbance at 340 nm measure over a 20 minute time period.

TABLE 18

CHANGE IN OD AFTER DIFFERENT INCUBATION TIMES OF THE RECEPTOR-LIGAND COMPLEX[1].

| 4-HYDROXY-PROPRANOLOL | (mA/min) | | | | |
|---|---|---|---|---|---|
| SAMPLE | 1' | 10' | 30' | 60' | 120' |
| 0.1 μg/ml | 3.918 | 2.256 | 2.083 | 1.034 | 4.197 |
| 1.0 μg/ml | 7.913 | 4.456 | 5.427 | 3.171 | 6.243 |
| 10 μg/ml | 12.875 | 12.855 | 13.720 | 10.210 | 12.759 |
| SLOPE[2] | 1.097 | 1.619 | 1.425 | 1.555 | 1.540 |
| INTERCEPT[2] | −0.120 | −0.580 | −0.433 | 09.533 | −0.522 |

[1]In this assay the release time was 5 min. and measurement time was 20 min.
[2]Slope and intercept were calculated according to the least squares method.

The similarity of the reaction statistics in Table 18 indicates that the antibody/ligand-enzyme complex was stable for at least 2 hours at room temperature, and that effective release could occur in the presence of free analyte during that time.

15.2.2. Optimizing Release time and Measurement Time

In addition to showing that the antibody/ligand-enzyme conjugate was stable for at least two hours, the assay was optimized for release time, i.e., the time after adding sample and NAD substrate before measuring the change in OD, and optimal measurement time, i.e., the time from start to finish for measuring the change in OD. The results of these optimization assays are shown in Tables 19 and 20.

TABLE 19

OPTIMIZING RELEASE TIME[1].

| 4-HYDROXY-PROPANOLOL CONCENTRATION | mOD/MIN AFTER | | |
|---|---|---|---|
| | 1 MINUTE | 3 MINUTES | 5 MINUTES |
| 0.1 ug/ml | 1.167 | 0.859 | 2.895 |
| 1.0 | 3.928 | 11.382 | 6.007 |
| 10.0 | 18.334 | 18.816 | 9.852 |
| SLOPE[2] | 1.743 | 0.857 | 1.0947 |
| INTERCEPT[2] | −0.665 | 0.213 | −0.117 |

[1]Antibody/ligand-enzyme complexes were incubated 10 sec. prior to adding sample; mOD/MIN (rate of absorbance change) was measured for 10 min.
[2]Slope and intercept were calculated according to the least squares method.

TABLE 20

OPTIMIZING READING TIME[1].

| 4-HYDROXY-PROPANOLOL CONCENTRATION | mOD/MIN AFTER | | |
|---|---|---|---|
| | 7 MINUTE | 10 MINUTES | 20 MINUTES |
| 0.1 ug/ml | 0.476 | 6.141 | 3.099 |
| 1.0 | 2.059 | 14.347 | 11.364 |
| 10.0 | 6.485 | 24.554 | 22.533 |
| SLOPE[2] | 1.481 | 1.0978 | 1.1362 |
| INTERCEPT[2] | −0.4771 | −0.1203 | −0.1633 |

[1]Antibody/ligand-enzyme complexes were incubated 10 min prior to addition of sample; the release time in this assay was 5 min.
[2]Slope and intercept were calculated according to the least squares method.

Under the condition of this assay, a release time of 5 min and a measurement time of NAD reduction for 10 min provide optimum results, with the best slope and intercept values.

16. EXAMPLE: HOMOGENEOUS RELEASE ASSAY FOR THIAZIDES

Thiazides are a class of diuretics, the most well known of which is hydrochlorothiazide. Detection of thiazides is important for medical treatment, particularly in emergency situations.

16.1. Materials and Methods

16.1.1. Ligand: Thiazide-Glucose-6-Phosphate Conjugate

The ligand-enzyme conjugate was prepared as follows: 15 mg of hydrochlorothiazide were dissolved in 0.5 ml of 5 N sodium hydroxide, and placed in boiling water for 30 minutes. The solution was cooled to room temperature and acidified with 1 ml of 6 N HCl. The tube was placed into an ice bath and 0.5 ml of 0.2M sodium nitrite added. The mixture was allowed to remain at 0° C. for 10 minutes, and then 0.5 ml of 7% ammonium sulfate were added.

The pH of the mixture was raised to between 5 and 6 using 100 μl of 0.5M sodium carbonate. In an ice bath 280 μl of the mixture were mixed immediately with 2.8 mg of glucose-6-phosphate dehydrogenase in 1 ml of 0.1M carbonate buffer, pH 9.0, containing 20 mg of NADH, 10 mg of glucose-6-phosphate and 300 μl of carbinol, and allowed to remain at 0° C. for 30 minutes. The reaction mixture was then dialyzed against 0.05M Tris buffer, pH 7.8, for 24 hours at 2°–8° C. with four changes of buffer.

16.1.2. Assay

Reagent A (160 μl) was anti-thiazide antibody (rabbit), 1 μl, in 147 μl Tris-HCl, pH 7.8, with 12 μl of 0.11M glucose-e-phosphate. Reagent B, (22 μl) was 10 μl of conjugate at 1:250 dilution in 12 of Tris-HCl buffer, pH 7.8, containing 3 mM magnesium. Reagents A and B were mixed and incubated for 5 minutes at room temperature. Samples were added in volumes of 10 μl. Incubation was continued at room temperature for 3 minutes, and then 8 μl of 0.1M NAD were added. Absorbance at 340 nm was measured for a 10 min period.

16.2. Results

Free hydrochlorothiazide in sample caused release of antibody from the ligand-enzyme conjugate, resulting in a dramatic shift in the rate of absorbance change. These results are summarized in Table 21.

TABLE 21

THIAZIDE RELEASE ASSAY.

| HYDROCHLOROTHIAZIDE CONCENTRATION (μg/ml) | RATE OF ABSORBANCE CHANGE (mAU/MIN) |
|---|---|
| 0.1 | 0.030 |
| 1.0 | 9.501 |
| 10 | 15.399 |

17. EXAMPLE: IDENTIFICATION OF A LOW AFFINITY ANALOG OF CONTININE BY ITS ABILITY TO COMPETE

The second principal urinary metabolite of nicotine, trans-3-hydroxycotinine, was tested for its ability to compete in the enzyme immunoassay for cotinine, which utilizes an antibody raised against carboxycotinine.

17.1. Materials and Methods

Trans-hydroxycotinine or cotinine were added to a synthetic urine matrix in levels from 0.1 to 5 μg/ml, and assayed in an ELISA for cotinine a mixture of cotinine and trans-hydroxycotinine in a 1:3 ratio were also assayed.

17.2. Results

Trans-hydroxycotine was only 10% as effective as cotinine at inhibiting binding in a cotinine ELISA. The enhanced binding (greater absolute OD values) in the presence of hydroxycotinine is an effect seen before in inhibition assays with low affinity ligands.

The ineffectiveness of hydroxycotinine as an inhibitor can also be seen in the inhibition curve of a 1:3 ratio of cotinine to hydroxycotinine. Although present in 3-fold excess, the hydroxycotinine cotinine combination is less inhibitory than cotinine alone. There is no observable additive inhibition by hydroxycotinine.

17.3. Discussion

The cotinine metabolite trans-hydroxycotinine; which differs from cotinine only by the presence of a hydroxyl group at C-3' in transorientation, binds antibody to cotinine with much lower affinity than cotinine. This is the characteristic necessary for a useful release ligand, and in fact, ligands prepared with trans-hydroxycotinine are useful in assays for cotinine (see Sections 6.–11., supra).

The phenomenon of enhanced binding, i.e., greater absolute O.D. values, in the presence of a low affinity analog is not well understood. It may be due to inhibition of cross-reactive antibodies. Nevertheless, enhancement of binding in the presence of low concentrations of a potential inhibition indicates useful low affinity ligand for release assays.

18. USE OF LOW AFFINITY CHROMATOGRAPHY FOR ISOLATION OF ANTIBODIES

Use of low affinity ligands for chromatography to purify antisera is advantageous because elusion under mild conditions yields higher antibody recovery. Such antibodies find particular use in release assays.

Isolation of antibodies to human chorionic gonadotropin (hCG) was accomplished using a column to which a crude extract of sheep gonadotropic hormones had been covalently bound. While these sheep hormones are not biologically active in humans, nor do they crossreact with anti-hCG, there remains enough sequence conservation, especially with sheep luteinizing hormone (sLH), to be able interact with antibodies to hCG under controlled conditions.

18.1. Materials and Methods

18.3.1. Preparation of Affinity Column

A crude extract of sheep pituitary gonadotropins was attached to sepharose using 1 g of cyanogen bromide activated sepharose 4B. The gel was placed in 1.6 ml of 0.1M carbonate buffer, pH 8.0, containing (0.5M sodium chloride. 24 mg of the crude extract were added and the material mixed for 3 hours at room temperature. The gel was centrifuged, supernatant discarded, and the gel resuspended in 0.01M Tris buffer, pH 8.0, and kept at 4° C. overnight.

The gel was centrifuged again, supernatant discarded, and the gel suspended in 10 ml of 0.01M Tris Buffer, pH 8.0, containing 0.2M glutamic acid. This suspension was incubated for 1 hour with mixing. Then the gel was packed into a 1×10 cm, column and washed sequentially with 0.1M acetate buffer, pH 4.0, 0.5M sodium chloride, and 0.1M sodium carbonate buffer, pH 8.0, containing 0.5M sodium ichloride. The column was then equilibrated with phosphate buffer, pH 7.0, containing 0.5M sodium chloride and 0.01% sodium azide.

18.1.2. Affinity Chromoatography

The column was primed with 1 µl of normal rabbit serum overnight at 4° C. the serum was eluted with phosphate buffered saline (PBS) followed by rinses with the buffers of pH 4 and 8. 1 ml of rabbit antiserum to hCG with a titer of 1:100,000 was applied to the column and allowed to sit 10 min. The column was sequentially eluted with PBS, pH 4 buffer and pH 8 buffer. Protein content of collected fractions was determined by the Lowry method, and anti-hCG activity by a solid phase competitive enzyme immunoassay.

18.2. Results

The chromatogram of protein content and antibody activity is shown in FIG. 14. The bulk of the protein eluted in the void volume of the column, while the majority of the antibody activity eluted just after the void volume in protein-poor fractions. A smaller protein peak eluted in pH 4 buffer, no protein eluted in pH 8 buffer.

The titer of the pooled fractions of antiserum was 1:91,200 and the protein content 2.7 mg, showing an activity recovery of 91%, far higher than that reported previously in the literature for affinity-purified antibodies. The specific activity of the starting antiserum was 2200 U/mg, while that of the pooled purified fractions was 37,000 U/mg, a 17-fold purification.

In order to show that the recovery of antibody by this method was not due to the properties of the Sepharose itself, a column of Sepharose 4B was prepared and normal rabbit serum and antiserum applied and eluted as described previously. All antibody activity elected in the void volume with the protein; none was retained on the column to be eluted afterward.

The antisera used in the experiment showed a 10% cross-reactivity with sLH after the affinity chromatography this level of cross-reactivity did not change.

18.3. Discussion

The purification of antibodies using low affinity analogs attached to affinity chromatography gels appears to permit efficient recovery of antibodies without denaturation and with enhanced specific activity for antigen.

Affinity purification schemes also provide a method to identify a low affinity analog by its ability to retard elution of specific antibody in a mild eluent. According to the above example, in a release assay for hCG, sheep gonadotropins may serve as ligands.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method of the detection of cotinine in a sample comprising:

(a) contacting a test sample with a receptor-ligand complex, wherein the ligand is 4-carboxynorcotinine having either a propyl or an isopropyl group, at the 1 N position and the receptor is an antibody generated against trans-4'-carboxynorcotinine, and (b) detecting dissociation of the receptor-ligand complex and binding of the receptor with cotinine which positively correlates with the presence of cotinine in the sample.

2. A method of the detection of cotinine in a sample comprising:

(a) forming a receptor-ligand complex wherein the ligand is 4-carboxynorcotinine having either a propyl or an isopropyl group at the 1 N position and the receptor is an antibody generated against trans-4'-carboxynorcotinine, (b) contacting a test sample with the complex, and (c) detecting dissociation of the receptor-ligand complex and binding of the receptor with cotinine which positively correlates with the presence of cotinine in the sample.

3. The method of claim 1 or 2 wherein detecting dissociation is by means of measuring a signal from a label associated with either receptor or ligand.

4. The method of claim 3 wherein the label is selected from the group consisting of an enzyme, a fluorophore, a chromophore, a latex particle, a chemiluminescent agent, radioisotope, a chelating complex, a dye, and colloidal gold.

5. The method of claim 1 or 2 in which the ligand or receptor is irreversibly absorbed to a solid phase support.

6. The method of claim 1 or 2 wherein the ligand has a propyl group at the 1N position.

7. The method of claim 1 or 2 wherein the ligand has an isopropyl group at the 1N position.

8. A kit for detecting the presence of cotinine in a sample comprising a preformed receptor-ligand complex, wherein the ligand is 4-carboxynorcotinine having either a propyl or an isopropyl group at the 1 N position and the receptor is an antibody generated against trans-4'-carboxynorcotinine, and means for detecting dissociation of the complex and release of the receptor which positively correlates with the presence of cotinine in the sample.

9. A kit for detecting the presence of cotinine in a sample comprising receptor and ligand for forming a receptor-ligand complex, wherein the ligand is 4-carboxynorcotinine having either a propyl or and isopropyl group atoms at the 1N position and the receptor is an antibody generated against trans-4'-carboxynorcotinine, and means for detecting dissociation of the complex and release of the receptor which positively correlates with the presence of cotinine in the sample.

10. The method of claim 8 or 9 wherein the ligand has a propyl group at the 1N position.

11. The method of claim 8 or 9 wherein the ligand has aa isopropyl group at the 1N position.

12. The kit of claim 8 or 9 wherein the means for detecting dissociation is a label which is conjugated to either the receptor or the ligand and which produces a detectable signal.

13. The kit of claim 12 wherein the intensity of the signal from the label is increased or decreased upon formation or dissociation of the complex.

14. The kit of claim 12 wherein the label is conjugated to the receptor and the ligand is conjugated to a carrier molecule and the ligand-carrier conjugate is absorbed to a solid phase support.

15. The kit of claim 12 wherein the label is selected from the group consisting of an enzyme, a fluorophore, a chromophore, a latex particle, a chemiluminescent agent, a radioisotope, a chelating complex, a dye, and colloidal gold.

16. The kit of claim 15 wherein the ligand or receptor is irreversibly absorbed to a solid support and the label is a colored latex particle.

17. The kit of claim 8 or 9 wherein the ligand or receptor is irreversibly absorbed to a solid phase support.

18. The kit of claim 17 wherein the receptor is irreversibly absorbed to a solid phase support and the means for detecting dissociation is a label which is conjugated to the ligand and which produces a detectable signal.

19. The kit of claim 18 wherein the label is selected from the group consisting of a fluorophore, a chromophore, a dye, a chemiluminescent agent, and a radioisotope.

20. The kit of claim 17 wherein the solid phase support is selected from the group consisting of a membrane and a microtiter plate.

* * * * *